United States Patent
Tandon et al.

(10) Patent No.: US 12,223,666 B2
(45) Date of Patent: *Feb. 11, 2025

(54) METHODS FOR OPTIMIZING THE PLANNING AND PLACEMENT OF PROBES IN THE BRAIN VIA MULTIMODAL 3D ANALYSES OF CEREBRAL ANATOMY

(71) Applicant: BOARD OF REGENTS OF THE UNIVERSITY OF TEXAS SYSTEM, Austin, TX (US)

(72) Inventors: Nitin Tandon, Houston, TX (US); Mehmet Kadipasaoglu, Houston, TX (US); Kevin Pham, Sugar Lang, TX (US); Cristian Donos, Bucharest (RO); Kiefer Forseth, Houston, TX (US); Patrick Sarahan Rollo, Houston, TX (US)

(73) Assignee: THE BOARD OF REGENTS OF THE UNIVERSITY OF TEXAS SYSTEM, Austin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/448,289

(22) Filed: Aug. 11, 2023

(65) Prior Publication Data
US 2024/0221192 A1 Jul. 4, 2024

Related U.S. Application Data

(63) Continuation of application No. 17/181,345, filed on Feb. 22, 2021, now Pat. No. 11,734,842.
(Continued)

(51) Int. Cl.
G06T 7/37 (2017.01)
A61B 34/10 (2016.01)
(Continued)

(52) U.S. Cl.
CPC ............... *G06T 7/37* (2017.01); *A61B 34/10* (2016.02); *G01R 33/5607* (2013.01); *G06T 7/11* (2017.01);
(Continued)

(58) Field of Classification Search
CPC ..... G06T 7/37; G06T 7/11; G06T 7/38; G06T 2207/10081; G06T 2207/10088;
(Continued)

(56) References Cited

U.S. PATENT DOCUMENTS 7,813,581 B1 * 10/2010 Fitzpatrick ............... G06T 5/70
348/169
10,149,618 B1 * 12/2018 Tandon ................. A61B 5/0077
(Continued)

FOREIGN PATENT DOCUMENTS

JP 2013-61196 4/2013
JP 2014-518516 7/2014
(Continued)

OTHER PUBLICATIONS

Puonti, Oula ("Fast and sequence adaptive whole-brain segmentation using parametric Bayesian modeling" NeuroImage (Year: 2016).*
(Continued)

*Primary Examiner* — Molly Wilburn
(74) *Attorney, Agent, or Firm* — Parker Highlander PLLC

(57) ABSTRACT

A method includes obtaining a first imaging scan and a second imaging scan of a single subject brain. The first imaging scan is converted to a first dataset, and the second imaging scan is converted to a second dataset. A sequence-adaptive multimodal segmentation algorithm is applied to the first dataset and the second dataset. The sequence-adaptive multimodal segmentation algorithm performs automatic intensity-based tissue classification to generate a first labelled dataset and a second labeled dataset. The first
(Continued)

labeled dataset and the second labeled dataset are automatically co-registered to each other to generate a transformation matrix based on the first labeled dataset and the second labeled dataset. The transformation matrix is applied to align the first dataset and the second dataset.

16 Claims, 16 Drawing Sheets

Related U.S. Application Data

(60) Provisional application No. 62/978,868, filed on Feb. 20, 2020.

(51) Int. Cl.
*G01R 33/56* (2006.01)
*G06T 7/11* (2017.01)
*G06T 7/38* (2017.01)

(52) U.S. Cl.
CPC .......... *G06T 7/38* (2017.01); *A61B 2034/102* (2016.02); *A61B 2034/107* (2016.02); *G06T 2207/10081* (2013.01); *G06T 2207/10088* (2013.01); *G06T 2207/10104* (2013.01); *G06T 2207/30016* (2013.01)

(58) Field of Classification Search
CPC . G06T 2207/10104; G06T 2207/30016; G06T 2207/10072; G06T 7/33; G06T 7/174; A61B 34/10; A61B 2034/102; A61B 2034/107; A61B 5/0042; A61B 5/37; A61B 5/6868; A61B 6/501; A61B 5/055; A61B 5/4836; A61B 5/0816; A61B 5/4815; A61B 5/4818; A61B 5/489; A61B 5/6814; A61B 6/5229; A61B 5/0035; A61B 5/4806; A61B 5/6891; A61B 5/7425; A61B 2034/105; A61B 2576/026; G01R 33/5607; G01R 33/5601; G01R 33/5608
See application file for complete search history.

(56) References Cited

U.S. PATENT DOCUMENTS

| | | | |
|---|---|---|---|
| 2008/0292194 A1* | 11/2008 | Schmidt | G06T 7/143 382/131 |
| 2010/0014732 A1* | 1/2010 | Vija | G06T 5/00 382/280 |
| 2011/0295515 A1 | 12/2011 | Grady et al. | |
| 2012/0093381 A1 | 4/2012 | Fan et al. | |
| 2015/0141804 A1 | 5/2015 | Rooney et al. | |
| 2016/0343127 A1* | 11/2016 | Miller | G06T 7/11 |
| 2017/0147908 A1 | 5/2017 | Chen et al. | |
| 2017/0193161 A1 | 7/2017 | Sapiro et al. | |
| 2020/0116808 A1* | 4/2020 | Taher | A61B 5/4064 |

FOREIGN PATENT DOCUMENTS

| | | |
|---|---|---|
| JP | 2016-517288 | 6/2016 |
| JP | 2019-500179 | 1/2019 |
| WO | WO 2012/135190 | 10/2012 |
| WO | WO 2014/139024 | 9/2014 |
| WO | WO 2015/010745 | 1/2015 |
| WO | WO 2017/072706 | 5/2017 |

OTHER PUBLICATIONS

Awate, Suyash P., et al. "Adaptive Markov modeling for mutual-information-based, unsupervised MRI brain-tissue classification." *Medical Image Analysis* 10.5 (2006): 726-739.
Conner, Christopher R., et al. "Category specific spatial dissociations of parallel processes underlying visual naming." *Cerebral Cortex* 24.10 (2014): 2741-2750.
Frangi, Alejandro F., et al. "Multiscale vessel enhancement filtering." *Medical Image Computing and Computer-Assisted Intervention—MICCAI'98: First International Conference Cambridge*, MA, USA, Oct. 11-13, 1998 Proceedings 1. Springer Berlin Heidelberg, 1998.
Freesurfer. Retrieved from: https://surfer.nmr.mgh.harvard.edu/fswiki/mri_tessellate; Feb. 21, 2021.
International Search Report mailed May 4, 2021, issued in counterpart International Application No. PCT/ US2021/019014.
Kadipasaoglu, C. M., et al. "Surface-based mixed effects multilevel analysis of grouped human electrocorticography." *Neuroimage* 101 (2014): 215-224.
Menze, Bjoern H., et al. "The multimodal brain tumor image segmentation benchmark (BRATS)." *IEEE transactions on medical imaging* 34.10 (2014): 1993-2024.
Partial Supplementary European Search Report issued in European Application No. 21757383.1, dated Feb. 13, 2024.
Puonti, Oula, Juan Eugenio Iglesias, and Koen Van Leemput. "Fast and sequence-adaptive whole-brain segmentation using parametric Bayesian modeling." *NeuroImage* 143 (2016): 235-249.
Puonti, Oula, Juan Eugenio Iglesias, and Koen Van Leemput. "Fast, sequence adaptive parcellation of brain MR using parametric models." *Medical Image Computing and Computer-Assisted Intervention—MICCAI 2013: 16th International Conference*, Nagoya, Japan, Sep. 22-26, 2013, Proceedings, Part I 16. Springer Berlin Heidelberg, 2013.
Saad, Ziad S., and Richard C. Reynolds. "Suma." *Neuroimage* 62.2 (2012): 768-773.
Vascular Modeling ToolKit software; Retrieved from VMTK: http://www.vmtk.org/vmtkscripts/vmtkmarchingcubes.html on Feb. 21, 2021.
Office Communication dated Oct. 29, 2024, issued in counterpart Japanese Application No. 2022-549631.

* cited by examiner

FIG. 8B
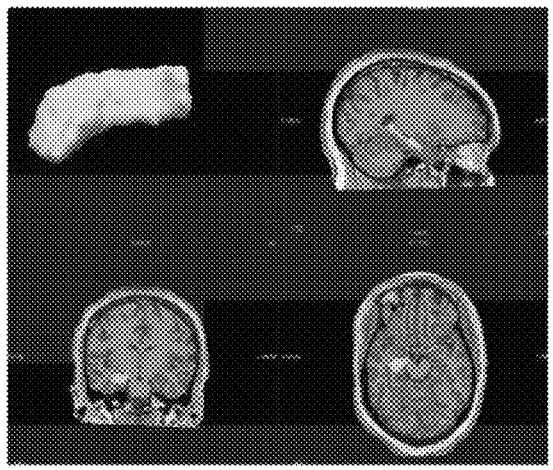
FIG. 8A
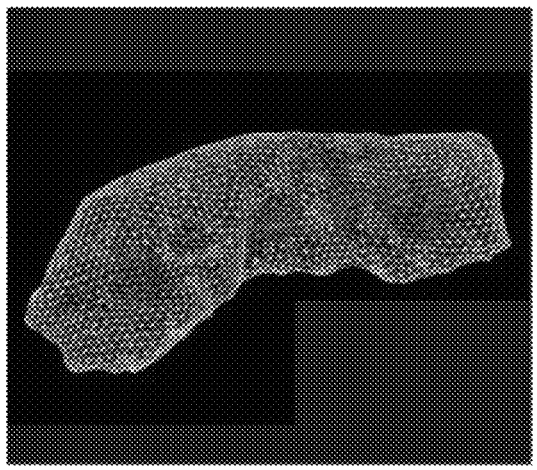
FIG. 8C
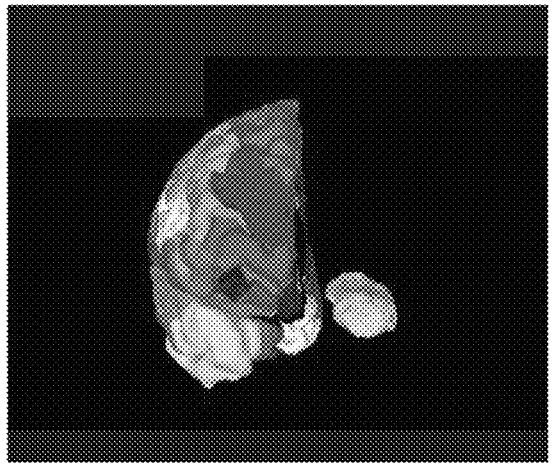
FIG. 8D
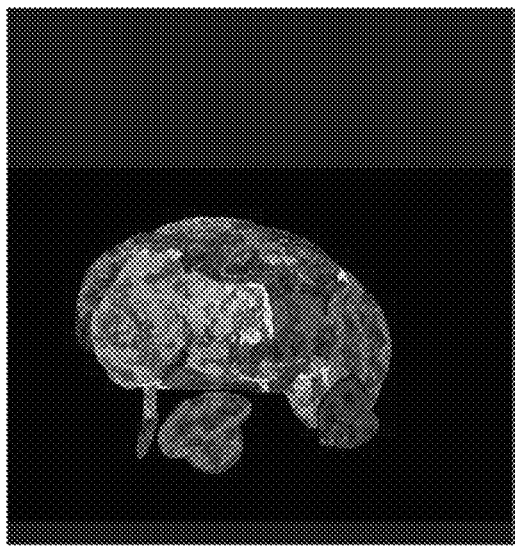
FIG. 8E
FIG. 8F FIG. 11A  FIG. 11B  FIG. 11C  FIG. 11D
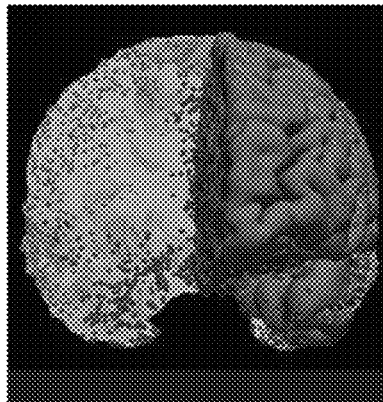   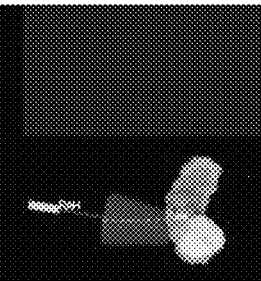
FIG. 11E
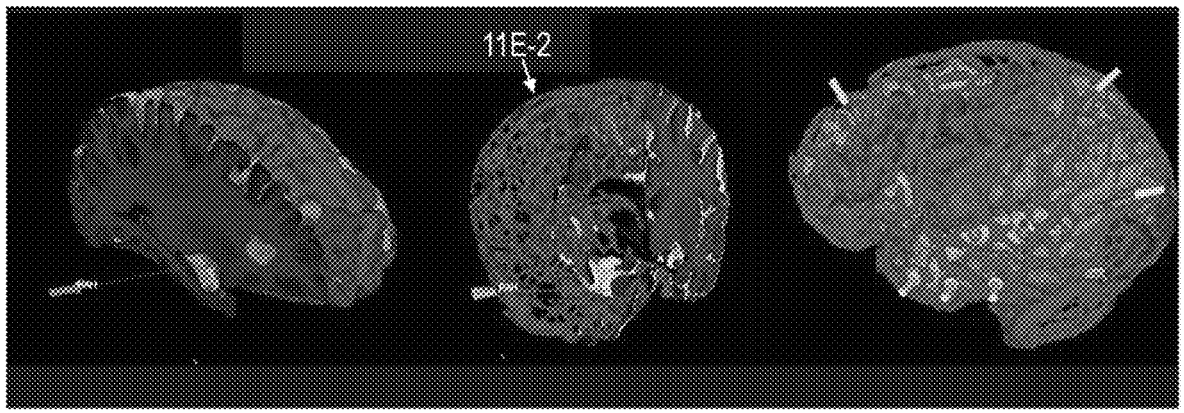
FIG. 11F
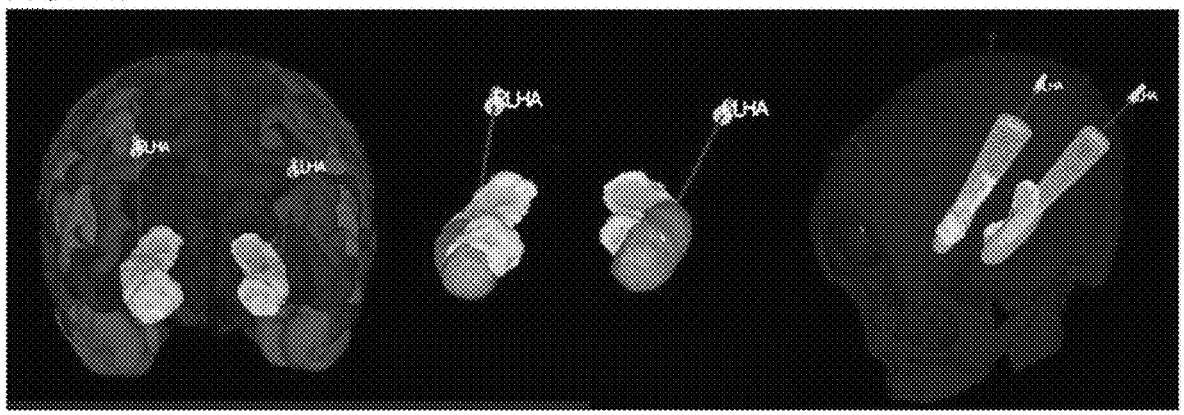

FIG. 12A
FIG. 12B  FIG. 12C
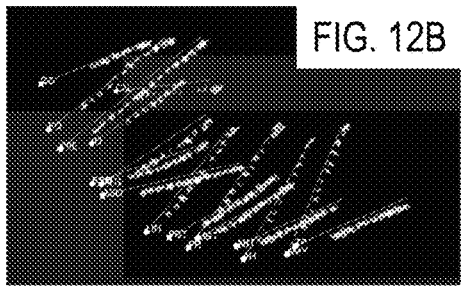 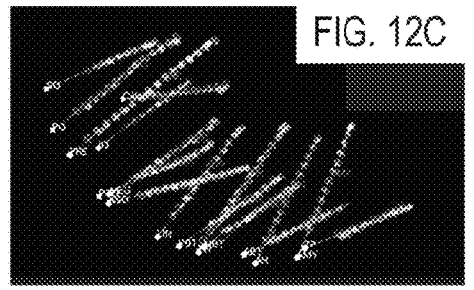
FIG. 12D
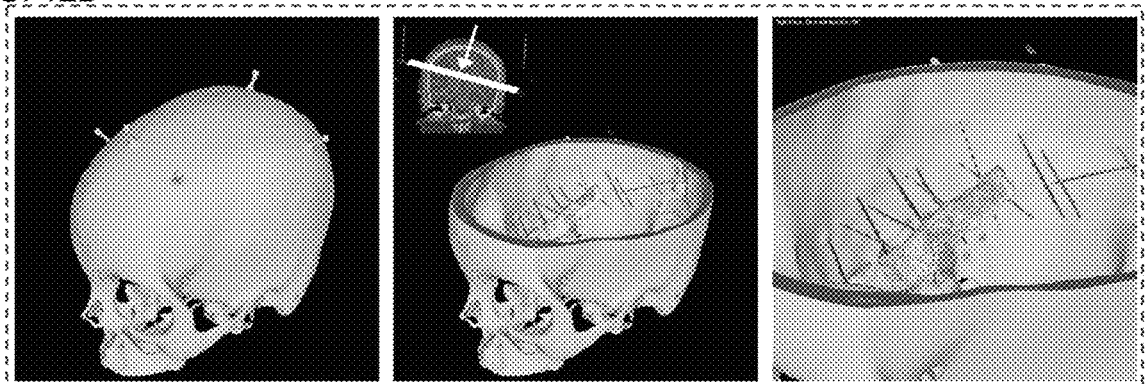
FIG. 12E
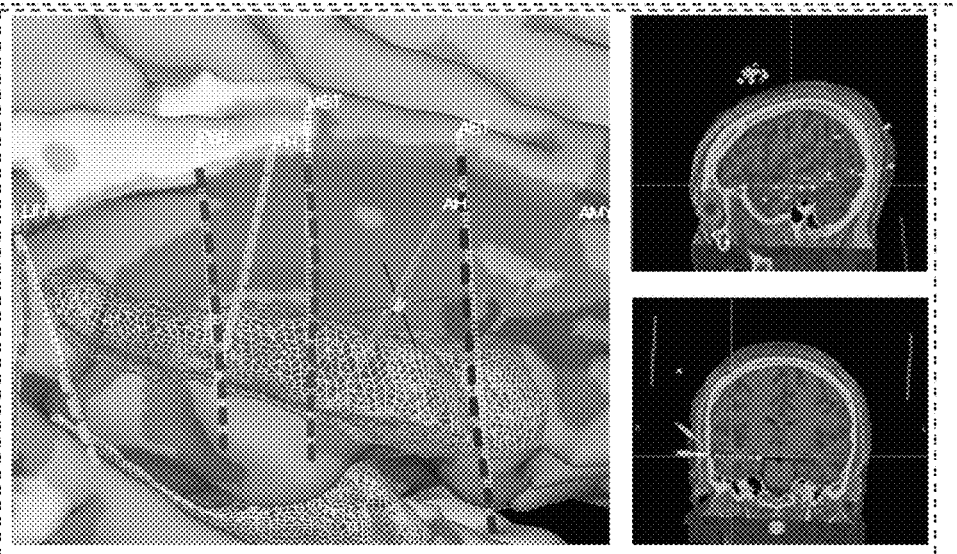

METHODS FOR OPTIMIZING THE PLANNING AND PLACEMENT OF PROBES IN THE BRAIN VIA MULTIMODAL 3D ANALYSES OF CEREBRAL ANATOMY

CROSS-REFERENCE TO RELATED APPLICATIONS

The present application is a continuation of U.S. patent application Ser. No. 17/181,345, filed Feb. 22, 2021, which claims priority to U.S. Provisional Patent Application No. 62/978,868, filed Feb. 20, 2020, entitled "Methods of Identifying and Avoiding Visual Deficits After Laser Interstitial Thermal Therapy for Mesial Temporal Lobe Epilepsy," which is hereby incorporated herein by reference in its entirety.

GOVERNMENT SUPPORT CLAUSE

This invention was made with government support under NS098981 awarded by National Institutes of Health. The government has certain rights in the invention.

BACKGROUND

Intracranial electrodes are implanted in patients for the recording of high spatiotemporal resolution intracranial electroencephalography (icEEG) data and for the modulation of neural circuits and systems. Patients undergo implantation most commonly for the evaluation of neurological diseases such epilepsy, movement disorders and psychiatric illnesses.

In a subset of patients with medically intractable epilepsy, seizure onsets can be localized to a definable focus, and in such exemplary circumstances, surgical interventions offer a potential for the cessation of further seizure activity through the direct resection, removal, or destruction of the pathological brain tissue, including minimally invasive approaches that include, but are not limited to, catheter-based tissue ablation. Unfortunately, in many cases, patients do not have a lesion that is identifiable using only non-invasive studies or evaluations, which can include studies of brain activity that include, but are not limited to, scalp electroencephalography (EEG) and magneto-encephalography (MEG), as well as anatomical imaging modalities used to identify structural lesions such as magnetic resonance imaging (MRI) or computed tomography (CT). Electrodes are also placed for the neuromodulation of epilepsy—currently that is either in the anterior nucleus of the thalamus or at the site of the genesis of seizures.

Movement disorders (Parkinson's disease, dystonia, essential tremor) are also common. The treatment of these disorders is often surgical, as medications generally result in undesirable side effects. Deep basal ganglia nuclei (e.g. subthalamic nucleus, globus pallidus interna and the VIM nucleus of the thalamus) and their associated white matter pathways are routinely targeted for these disorders.

Psychiatric disorders are rapidly becoming targeted for neuromodulation in cases where medications are ineffective—these include cases of treatment resistant depression, obsessive compulsive disorder, post-traumatic stress disorders and eating disorders.

In such exemplary patients, implantation of subdural electrodes (SDEs) and/or stereo-electroencephalography (SEEG) electrodes and/or other probes or catheters or recording devices is a common strategy used to precisely define the relationships between healthy and/or eloquent brain regions and the pathologic brain regions that may underlie a putative pathological network, for diagnosis or for stimulation to cause neuromodulation.

SUMMARY

A method includes obtaining a first imaging scan and a second imaging scan of a single subject brain. The first imaging scan is converted to a first dataset, and the second imaging scan is converted to a second dataset. A sequence-adaptive multimodal segmentation algorithm is applied to the first dataset and the second dataset. The sequence-adaptive multimodal segmentation algorithm performs automatic intensity-based tissue classification to generate a first labelled dataset and a second labeled dataset. The first labeled dataset and the second labeled dataset are automatically co-registered to each other to generate a transformation matrix based on the first labeled dataset and the second labeled dataset. The transformation matrix is applied to align the first dataset and the second dataset.

A non-transitory computer-readable medium encoded with instructions that are executable by one or more processors to obtain a first imaging scan and a second imaging scan of a single subject brain, and to convert the first imaging scan to a first dataset, and the second imaging scan to a second dataset. The instructions are also executable by the one or more processors to apply a sequence-adaptive multimodal segmentation algorithm to the first dataset and the second dataset, wherein the sequence-adaptive multimodal segmentation algorithm performs automatic intensity-based tissue classification to generate a first labelled dataset and a second labeled dataset. The instructions are further executable by the one or more processors to automatically co-register the first labeled dataset and the second labeled dataset to each other to generate a transformation matrix based on the first labeled dataset and the second labeled dataset. The instructions are yet further executable by the one or more processors to apply the transformation matrix to align the first dataset and the second dataset.

A system includes one or more processors and a memory. The memory is coupled to the one or more processors, and stores instructions. The instructions configure the one or more processors to obtain a first imaging scan and a second imaging scan of a subject brain, and to convert the first imaging scan to a first dataset, and the second imaging scan to a second dataset. The instructions also configure the one or more processors to apply a sequence-adaptive multimodal segmentation algorithm to the first dataset and the second dataset, wherein the sequence-adaptive multimodal segmentation algorithm performs automatic intensity-based tissue classification to generate a first labelled dataset and a second labeled dataset. The instructions further configure the one or more processors to automatically co-register the first labeled dataset and the second labeled dataset to each other to generate a transformation matrix based on the first labeled dataset and the second labeled dataset. The instructions yet further configure the one or more processors to apply the transformation matrix to align the first dataset and the second dataset.

BRIEF DESCRIPTION OF THE DRAWINGS

For a detailed description of various examples, reference will now be made to the accompanying drawings in which:

FIGS. 8A-8F show a pictorial representation depicting generation of 2D/3D surface models of the hippocampus as well as the thalamus in accordance with the present disclosure.

FIGS. 11A-11H, 11J-11N, and 11P-11R show an example of population-derived anatomical targeting for electrode or penetrating probe implantation in accordance with the present disclosure.

FIGS. 12A-12E show pictorial representations of automated electrode localization and labelling.

DETAILED DESCRIPTION

Figure 1:
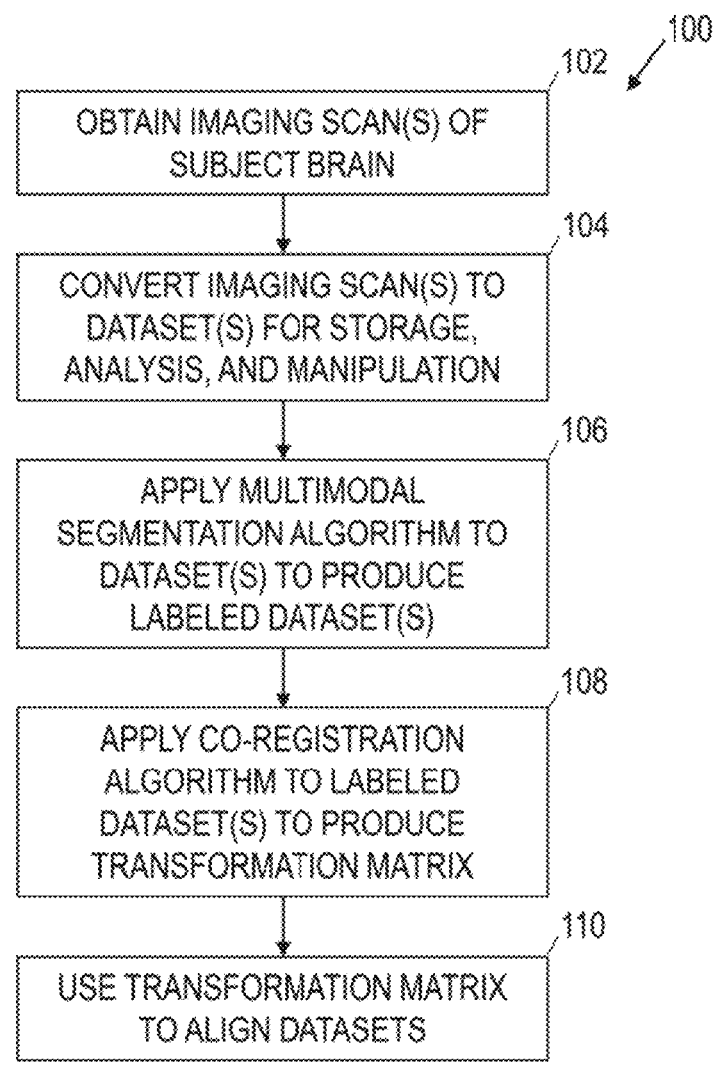
FIG. 1 shows a flow diagram for a method for co-registration of brain imaging scans in accordance with the present disclosure.

Certain terms have been used throughout this description and claims to refer to particular system components. As one skilled in the art will appreciate, different parties may refer to a component by different names. This document does not intend to distinguish between components that differ in name but not function. In this disclosure and claims, the terms "including" and "comprising" are used in an open-ended fashion, and thus should be interpreted to mean "including, but not limited to . . . ." Also, the term "couple" or "couples" is intended to mean either an indirect or direct wired or wireless connection. Thus, if a first device couples to a second device, that connection may be through a direct connection or through an indirect connection via other devices and connections. The recitation "based on" is intended to mean "based at least in part on." Therefore, if X is based on Y, X may be a function of Y and any number of other factors.

There are a number of clinical justifications for implanting electrodes or other medical devices in the brain, and focal epilepsy provides a single exemplary condition, that is focused on herein for illustrative purposes. In all such patients that meet the criteria for invasive monitoring or interventional procedure, the patient's clinical course can be broadly classified into three stages: 1) planning; 2) data acquisition; and 3) intervention. In general, during planning stages, patients undergo high-resolution anatomical imaging using MRI, which may also be performed following injection of a contrast agent into the blood stream for the enhanced imaging of blood vessels. More recently, with improvements in computational modeling technologies, data from these imaging scans may be used to generate 2D and 3D models of the patient's cerebral anatomy, which can better inform surgeons and clinicians planning subsequent surgical interventions while accounting for critical or vital anatomical structures.

Following planning, the patients will undergo intracranial electrode implantation, following which post-operative imaging is typically acquired (e.g. CT brain scan) in order to precisely and accurately relate the implanted electrodes to the patient's cortical anatomy. Similarly, 2D and/or 3D computational models of the implanted electrodes or probes can be generated from the repeat imaging scans, and used to relate the electrophysiological data acquired to the underlying cortical anatomy once the different (pre- and post-implant) imaging data are brought into co-registration with each other (e.g. aligned to a common coordinate space).

In the intervention stage, the data gathered from stages 1 and 2 (planning and implantation) have been used as part of the patient's comprehensive clinical evaluation to determine whether a putative pathological focus can be localized, and if so, what its relationships to critical and non-critical brain structures may be. This information is used by the surgeon to optimize a final surgical plan for the removal of seizure foci that minimizes injury to healthy or vital brain regions.

In each of these stages, precision and accuracy are paramount to ensure that the patient does not sustain any transient or permanent adverse neurological outcome that could have otherwise been avoided. Despite the numerous technical, imaging, and computational advances that have been developed in the past 20 years, significant technological hurdles remain. These include challenges for accurate co-registration of different imaging modalities; for the automated planning of electrode implantation; for methods using non-invasive imaging data only to minimize risk of injury to critical structures (e.g. blood vessels); for the automated and/or semi-automated integration of post-implantation imaging data with neuro-anatomical and functional data to inform potential surgical interventions. The methods and systems disclosed herein overcome the aforementioned limitations using the novel approaches described below.

Embodiments of the present disclosure relate to the robust and accurate co-registration of different brain imaging modalities. In particular, the present disclosure describes a novel application of a sequence-adaptive multimodal segmentation algorithm to the same and/or different imaging modalities used for the acquisition of brain imaging to achieve accurate within-subject multi-modal co-registration of these imaging modalities in a robust and automated fashion. The sequence-adaptive multimodal segmentation algorithm is applied to 3D datasets generated from the original brain imaging scans performed on the patient, which may include but are not limited to data formats as described by the Neuroimaging Informatics Technology Initiative (NIFTI), and which are generated from the imaging files of patient's brain scan, an exemplary embodiment of which could be images stored according to the standards defined by the Digital Imaging and Communications in Medicine (DICOM) standard. The sequence-adaptive multimodal segmentation algorithm is applied to the datasets without the need of further or additional pre-processing (including but not limited to intensity normalization and/or volume conformation) to generate a new labeled segmentation dataset of the same volume and geometry of the original datasets but one in which each voxel (i.e., 3D pixel) has had its original intensity value replaced by a number that relates to a unique anatomical region and/or the probability of that voxel belonging to various brain regions (an exemplary embodiment of which may include a probabilistic distribution of brain regions as defined by a template or reference atlas). The segmented dataset is then utilized as the "moving" input to the co-registration algorithm to be aligned to an equivalently segmented "target" dataset generated from the same and/or different imaging modality on the same patient. The co-registration algorithm will also generate as part of the computational output a transformation matrix that describes the mathematical operations needed to exactly replicate the alignment between the input "moving" and "target" datasets in a symmetric fashion—that is in both a forward (i.e., align the "moving" dataset to the "target" dataset) and a backward (i.e., align the "target" dataset to the "forward" dataset) fashion. Once the transformation matrix is generated, the transformation matrix can be applied to any dataset that shares the volume geometry of the original moving dataset to bring it into alignment with the original target dataset. This disclosure describes an entirely new application of segmentation algorithms to co-register imaging datasets taken in the same subject using the same or different imaging modalities (e.g. MRI and CT) based on transformation matrices generated using segmentation, which provides a technological improvement that significantly advances the prior state of the art for within-subject multi-modal co-registration of brain images. Implementations of this disclosure result in satisfactory outcomes despite the presence of imaging features that would be a common cause of failure in other currently existing co-registration methods, which include but are not limited to anatomical defects, lesions and/or masses, foreign bodies, hemorrhage and/or intensity differences between imaging datasets and/or differences in the imaging pulse-sequence used and/or scanner platform parameter on which the image was acquired.

Embodiments of the present disclosure relate to methods of using extracranial boundary layers, generated by a sequence-adaptive multimodal segmentation algorithm to generate anatomically accurate skin and skull models to facilitate the pre-surgical planning and post-implantation localization of sEEG electrodes. The segmentation of extracranial boundary elements directly from CT imaging is an entirely novel approach that is an improvement on prior methods. The generation of a skull boundary layer using the methods applied to a T1-weighted MRI dataset are also entirely new approaches to the field that demonstrate improvements to current methods of boundary element modelling used to estimate these layers. These improvements provide tangible benefits to the planning of surgical electrode implantation by providing the skull-brain and skin-skull boundary layer for electrode implantation.

Embodiments of the present disclosure relate to methods of using the segmentations of cerebrospinal fluid (CSF) volumes, as well as gray and white matter cortical layers, as masks to aid in the segmentation of blood vessels from 3D brain imaging datasets which include but are not limited to contrast-weighted T1 MR imaging. In some exemplary embodiments, MR imaging datasets may have their intensity values up-scaled so as to better separate high-intensity voxels likely to reflect blood vessels from surrounding tissues with similar (but lower) intensity values (e.g., white matter tracts or from partial-volume averaging). The use of CSF boundary layers to mask and constrain the parameter space for blood vessel segmentation using up-scaled contrast MRIs is a novel approach for facilitating the segmentation of cerebral vasculature.

Embodiments of the disclosure relate to methods of applying, in some exemplary embodiments, a multi-scale Hessian-based filter to segment blood-vessels from the aforementioned CSF-, gray-, and white-matter-masked datasets.

Embodiments of the present disclosure relate to methods of generating 2D/3D anatomical mesh models of a patient's hippocampus, amygdala, as well as other subcortical structures, and for generating standardized versions of these anatomical meshes derived from high-resolution template volumes of the same.

Embodiments of the present disclosure relate to methods of determining optimal trajectories for the implantation of electrodes or penetrating probes into the brain using loss-functions and/or risk metrics defined in relation to the segmented blood vessel volumes.

Embodiments of the present disclosure relate to methods of 2D/3D visualization of cerebral vasculature. In some exemplary embodiments, the aforementioned visualizations will require reconstructing discontinuities in blood vessel volumes. In some exemplary embodiments, this visualization is achieved using algorithms originally developed for diffusion tensor imaging. In such exemplary embodiments, digital image intensity modulation is applied to the blood vessel volumes, constrained to specific directional gradients in 3D space that in some embodiments is performed using Hessian or Tensor based decompositions, to mimic anisotropic diffusion in 3D imaging volumes. These datasets can subsequently be processed by diffusion tensor imaging toolboxes to model and predict the connections between similar yet discontinuous imaging features. In this fashion, for example, likely connections between similar voxels that have become discontinuous due to low signal-to-noise ratios or processing artifacts can be re-modeled and visualized (e.g. for blood vessels in 3D imaging volumes). In this fashion, for example, continuous blood vessels can be reconstructed from discontinuous datasets.

Embodiments of the present disclosure relate to methods of generating topologically accurate 2D/3D surface-based representations and/or anatomical mesh models of the hippocampus, amygdala, thalamus, basal ganglia, and other subcortical structures for use in surgical planning. Parcellations of cortical regions are also generated, and any one of these structures can be visualized and manipulated independently, with respect to adjacent structures and contralateral structures. Further, using population-based atlases and templates, standardized surface models of these subcortical and/or other deep structures may also be generated, which will enable the translation and application of surface-based co-registration and analyses techniques that were originally developed for cortical-based inter-subject analyses and shown to yield significant improvements to accuracy and results. These methods are an entirely new contribution to the field which will provide significant improvements in the modeling of hippocampal and/or other subcortical region pathology or understanding of hippocampal/amygdala or other deep brain structure pathology through direct visualization or through the representation of functional or electrographic data upon the mesh surface model, or for the modeling of electrode or penetrating probe or catheter implantation to these regions.

Embodiments of the present disclosure relate to methods of aligning trajectories, obtained from a robotic, mechanical, or human implantation device or process, to the subject anatomical T1 MR imaging using the volume geometry and transformation matrices obtained from the subject's contrast-weighted T1 MR imaging.

Embodiments of the present disclosure relate to methods of precisely identifying the anatomical targets to be implanted or targeted using automated parcellation techniques, as well as linear and/or non-linear deformation algorithms to warp the subject brain to a standard template space in which targets are previously defined based on anatomy and vice-versa.

Embodiments of the present disclosure relate to methods of precisely identifying the anatomical target to be implanted or targeted using a prior probability distribution derived from a previously implanted population.

Embodiments of the present disclosure relate to assigning anatomical targets to motivate unsupervised design of implantation trajectories using depth electrodes placed for the identification of epilepsy directed by specific semiological features of seizures or the characterization of the epilepsy. This may apply to the placement of laser probes, brain electrodes for recording or for modulation, stereotactic biopsy probes, injection of biological, cellular, genetic or chemical materials into the brain via trajectories using anatomical constraints and prior implant cases.

Embodiments of the present disclosure relate to methods of generating 3D surface models of predicted ablation volumes (i.e. expected volume of hippocampal tissue to be affected) using a prior probability distribution derived from previous laser ablation volumes across a population. This is a new contribution to the field that will improve the pre-surgical planning and informed trajectory modeling for subsequent laser-ablation or other similar catheter-based therapies.

Embodiments of the present disclosure relate to automated techniques to identify and avoid damage to white matter pathways (identified via either deterministic or probabilistic tractography derived from diffusion imaging) involved in crucial functions such as motor, sensory, auditory, or visual processes.

Embodiments of the present disclosure relate to methods of automated segmentation and localization of sEEG electrodes using intensity-upscaling of post-implantation CT Brain imaging datasets and volume-based clustering algorithms of the resulting metal artifacts. Trajectories from the robotic implantation device, previously aligned to the same imaging space, are fitted using linear regression modeling to facilitate the identification of metal electrode artifacts from noise. Line-fitting models enable the automated method to account for deviations in electrode locations. Artifact clusters identified using 3D volumetric clustering search algorithms are iteratively searched while masking out any cortical region not within the current cluster of interest, to ensure overlapping or conflated artifacts can be resolved. Identified clusters are aligned to the robotic trajectories using information about the parallel relationships between the trajectory path and trajectories of the identified clusters, as well as information about the centroid of the clusters to re-fit the trajectories once sufficient numbers of electrodes are identified. Real-time visualization of the search algorithm enables concurrent updates of cluster search results for informational and debugging purposes.

Embodiments of the present disclosure relate to methods for verification of an implantation plan of multiple stereotactic depth probes along oblique trajectories, which is aided by simultaneous visualization of a cortical mesh model of surface topology and deep anatomy revealed by structural magnetic resonance imaging, sliced along a plane colinear with the proposed trajectory. The slicing of the brain surface in any given plane enables the visualization of deep buried cortex in 3D and also enables rapid confirmation of the surgical plan by clinicians.

Embodiments of the present disclosure relate to methods of manipulating 3D spatial geometry to selectively visualize or interact with differing surface models (e.g. skin, skull, blood vessel, brain, hippocampus, amygdala, etc.) along any plane. Surfaces can be rendered selectively traversable along any plane. Visualizations of parcellations or intracranial EEG activity can likewise be rendered along or deep to the visualized surfaces, along any plane.

Embodiments of the present disclosure relate to methods for transforming intracranial electroencephalography (icEEG) activity from surface-based representations to DICOM or 3D dataset formats, which depict the user-defined activations of interest constrained to the underlying cortical ribbon reflecting the likely gray matter regions responsible for this activation.

Embodiments of the present disclosure relate to methods for performing empirical source-localization estimates to model the unique neural generators of the recorded icEEG data.

Using the methods disclosed herein, implanted structures are resolved automatically with a template matching search in post-surgical imaging along known planned trajectories. This provides clinical staff with the final location for all implanted materials in automated fashion (without manually identifying each electrode for example) and enables the rigorous measurement of surgical accuracy. In a specific application, the methods disclosed herein help to avoid visual deficits after laser interstitial thermal therapy for mesial temporal lobe epilepsy.

FIG. 1 shows a flow diagram for a method 100 for co-registration of brain imaging scans obtained for a subject by different imaging modalities. Though depicted sequentially as a matter of convenience, at least some of the actions shown can be performed in a different order and/or performed in parallel. Additionally, some implementations may perform only some of the actions shown. Operations of the method 100 may be performed by a computing system as disclosed herein.

In block 102, one or more imaging scans of a subject's brain are obtained. The imaging scans may be performed with a scanning modality such as magnetic resonance imaging sequences (MRI), computerized tomography (CT) sequences, magnetoencephalography (MEG), positron emission tomography (PET), or any combination thereof.

In block 104, the imaging scans are converted into a file format/dataset that can be used for storage, analysis, and manipulation of the brain imaging data contained within the imaging scan. For example, the imaging scans may be converted to the NIFTI format.

In block 106, each dataset produced in block 104 is provided as input to a sequence-adaptive multimodal segmentation algorithm to generate labeled parcellation and segmentation datasets. In general, the segmentation algorithm proceeds by aligning a probabilistic atlas to the patient dataset. The atlas, in one exemplary embodiment, helps assign the probability of a specific brain region label to any voxel of the dataset given the intensity value of the voxel. In one exemplary embodiment, this could be achieved by using a Bayesian analysis where the atlas provides prior probabilities of a voxel belonging to a specific tissue class. The algorithm may then utilize, as an example, likelihood distributions to define relationships between a given brain region label and the distribution of intensity values in the voxels of that dataset. The term tissue classifications may refer to white matter, gray matter, cerebrospinal fluid, brain tumor and/or other brain regions. The term alignment used here may refer to either linear or non-linear methods. For examples of the use of a segmentation algorithm for the sequence-adaptive segmentation of brain MRI see, for example: Puonti O., Iglesias J. E., Van Leemput K. (2013) Fast, Sequence Adaptive Parcellation of Brain MR Using Parametric Models. In: Mori K., Sakuma I., Sato Y., Barillot C., Navab N. (eds) Medical Image Computing and Computer-Assisted Intervention—MICCAI 2013. MICCAI 2013. Lecture Notes in Computer Science, vol 8149. Springer, Berlin, Heidelberg. https://doi.org/10.1007/978-3-642-40811-3_91. Application of the sequencing algorithm for the co-registration of different imaging modalities is unknown in the art (e.g. between MRI and CT), and is a novel application here. Notably, the application of this algorithm to achieve fast, accurate, and robust co-registration between different imaging modalities (an exemplary embodiment of which may be co-registration of MRI and CT imaging scans) is a significant improvement over the prior state of the art. In the labeled datasets, imaging data (an exemplar data unit of imaging data is a 3D pixel of 1 mm×1 mm×1 mm resolution (referred to herein as a voxel), are replaced by numeric labels assigned according to extra- and intra-cranial structures represented. In various embodiments, a voxel can be of any dimensions deemed useful by the user. the term parcellations are used to refer to labelled cortical regions, while the term segmentations refer to labelled subcortical regions. In the present disclosure, these two terms are used interchangeably to refer to any labeled cortical or subcortical region.

in block 108, the labeled datasets are input to a co-registration algorithm whereby any two datasets are aligned to the coordinate space of each other, and from which a mathematical transformation matrix is generated that enables this coordinate transformation to be applied to any other dataset that shares the volume geometry of either one of the two input datasets in order to align this other dataset to the coordinate space of the second input dataset. The transformation matrix may be, in one exemplary embodiment, a 4×4 matrix, M, that defines a linear, rigid, and/or affine transformation of a point p to another point p' as defined by the equation p'=Mp. In this example, the point p defines the location of one voxel in a dataset, using a column vector comprising x,y,z coordinates of voxel and the number 1. For example, p=(x,y,z,1). The matrix-vector product multiplies the vector column from matrix M with the corresponding (x,y,z,1) values from column vector p. Summing the scalar-vector products generates the output vector p': (x', y',z',1). In such an example, the upper 3×4 elements of the matrix M, may contain real numbers used to store a combination of translations, rotations, scales, and/or shears (among other operations) that are applied to p. The final row in this exemplar would be (0 0 0 1). A transformation matrix of this form may be generated using one or more of a variety of neuroimaging analysis software. The use of a labeled dataset with parcellations/segmentations as input to co-registration, specifically in the case of CT imaging, overcomes many of the limitations of the prior state of the art (e.g., relating to intensity scaling differences or tissue boundary difference), and generates reliably accurate co-registration even in presence of anatomical defects (e.g. brain stroke), brain lesions (e.g. tumors) or other imaging artifacts.

In block 110, the datasets generated in block 104 are aligned to each other using the transformation matrix.

Figure 2:
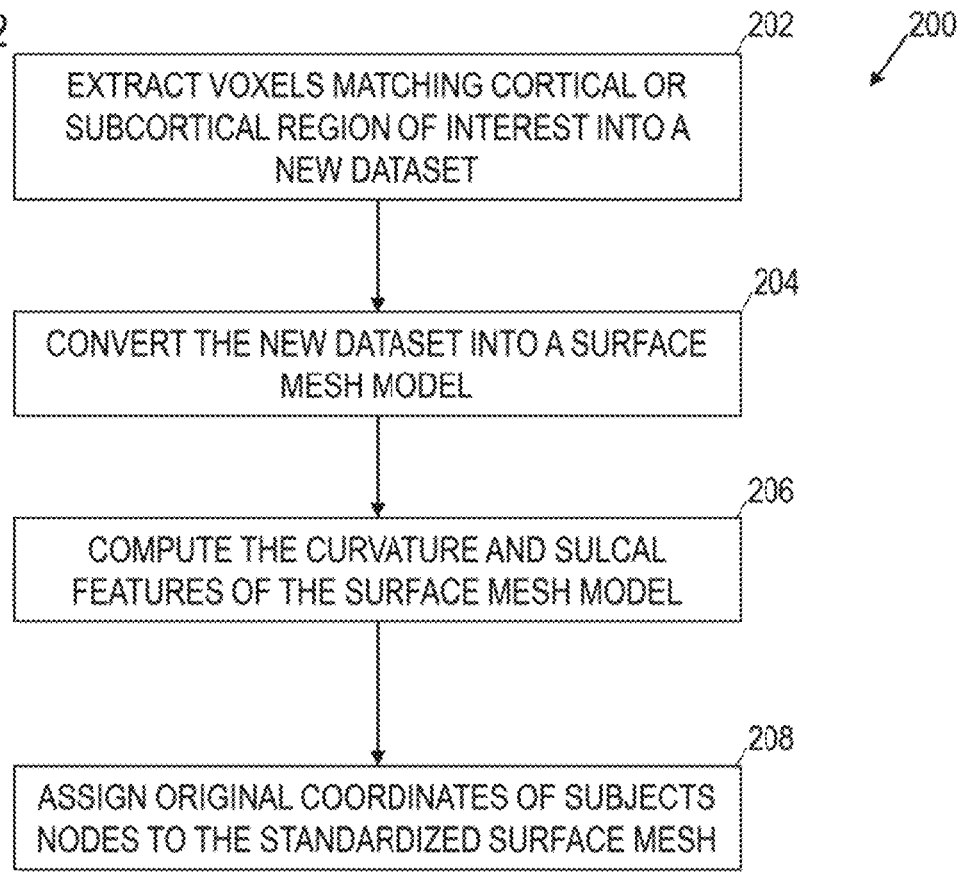
FIG. 2 shows a flow diagram for a method for generation of surface models of cortical and subcortical brain regions in accordance with the present disclosure.

FIG. 2 shows a flow diagram for a method 200 for generation of surface models of cortical and subcortical brain regions in accordance with the present disclosure. Though depicted sequentially as a matter of convenience, at least some of the actions shown can be performed in a different order and/or performed in parallel. Additionally, some implementations may perform only some of the actions shown. Operations of the method 200 may be performed by a computing system as disclosed herein on a labeled dataset as produced by the method 100.

The surface models generated by the method 200 include standardized mesh models derived from a population-level atlas that allows for a point-to-point correspondence between any point on one subject's surface with the same point on the surface in another subject.

In block 202, all voxels matching labeled values for the cortical or subcortical region of interest are extracted into a new 3D dataset containing only those voxels of interest. For example, the new dataset may include the right hippocampus as identified during the segmentation processing of the method 100.

In block 204, the 3D dataset of the segmented cortical or subcortical region of interest formed in block 202 is converted into a surface mesh model using standard volume-to-surface conversion. In general, standard volume-to-surface conversions may be achieved using existing open-source neuroimaging software. General and exemplary embodiments of such methods include volume binarization followed by surface tessellation using the binarized value to generate a mesh (e.g., as provided by Freesurfer: https://surfer.nmr.mgh.harvard.edu/fswiki/mri_tessellate) or a marching cubes algorithm as made available by the open source Vascular Modeling ToolKit software (VMTK: http://www.vmtk.org/vmtkscripts/vmtkmarchingcubes.html). In one exemplary embodiment a surface/anatomical mesh model may be defined as points in 3D space that are joined by lines to form triangles, each of which has a 2D face and which are combined according to a specific volume geometry to form a topologically accurate representation of the object modeled. The surface/anatomical mesh model may be, in one exemplary embodiment, a 2D model (e.g., a plane) that is then folded in 3D space to depict a 3D object (e.g., a brain surface).

In block 206, the curvature and sulcal features of the resulting surface model are computed, which are then used to nonlinearly align an inflated version of the surface model to match a high-resolution atlas of the same region generated from labeled population data. In this context, a high-resolution atlas may refer to a reference template pattern of cortical curvature data that, in some exemplary embodiments, was previously prepared as an average pattern computed from a group of representative subjects and made available as part of the standard repository. In other exemplary embodiments such template data may be generated using selected subject populations (e.g., patients at a particular institution operated on in a certain way).

In block 208, a standardized surface mesh that is already in alignment with the atlas, is overlaid on the subject's original surface model, and coordinates of this standardized surface mesh are replaced by a resampling of the surrounding coordinates of the subject's native coordinate space. The surface meshes comprise many thousands of points in space called nodes, connected by lines to form triangles, whose faces form the mesh of the surface model. In the context of a standardized surface, the mesh model comprises a fixed number of nodes and maintains a specific node-to-atlas region correspondence (i.e., each node corresponds to the same region in the atlas), and this correspondence may be preserved across subjects. To preserve the correspondence, for each subject, the standardized surface mesh and the subject's own original surface mesh are both deformed in a non-linear fashion to align to a spherical template mesh derived from the aforementioned high-resolution population atlas. Both subject and standardized meshes are warped to maximize the overlap between sulcal and curvature patterns. Once both subject and standardized surface meshes are aligned to the template atlas, and are therefore in alignment with each other, the nodes of the standardized surface mesh are assigned an average of the coordinates of a subset of the surrounding nodes from the subject's original surface mesh (an exemplary embodiment of which could be the 4 nearest nodes). In this fashion, the standardized surface is warped to the subject's anatomical coordinate space while both are aligned to the template, thereby preserving the one-to-one correspondence of the standardized surface with the template atlas. Once deflated from the spherical configuration used during co-registration, the standardized surface mesh assumes the topology of the subject's own anatomy, while continuing to maintain its one-to-one correspondence between node and anatomical atlas identity. In this fashion, a surface-based comparison can be performed across subjects with high levels of accuracy simply by comparing a specific node to the same node between surfaces.

The operations of the method 200 may be repeated for the contra-lateral hemispheric region, and for any other additional cortical or subcortical or other labeled/segmented or parcellated brain surface to be generated. For information regarding generation of a standardized surface for cortical surfaces see, for example, Saad, Z. S., Reynolds, R. C., 2012. Suma. NeuroImage 62, 768-773. http://dx.doi.org/10.1016/j.neuroimage.2011.09.016.; Kadipasaoglu C M, Baboyan V G, Conner C R, Chen G, Saad Z S, Tandon N. Surface-based mixed effects multilevel analysis of grouped human electrocorticography. Neuroimage. 2014 Nov. 1; 101:215-24. doi: 10.1016/j.neuroimage.2014.07.006. Epub 2014 Jul. 12. PMID: 25019677). However, no such method is known for generating standardized surface-based meshes of subcortical regions. Exemplary embodiments of such regions may include the hippocampus, amygdala, thalamic nuclei and basal ganglia. Such surface models could be used to create standardized subcortical surfaces for individual anatomy, allowing for concordance of these subcortical structures between individuals in a manner not previously done.

Use of the method 200 for brain regions not conventionally included in surface-based modeling or analyses (e.g. hippocampal and/or amygdala and/or subcortical regions), in conjunction with the use of high-resolution anatomical atlases of the regions to enable the generation of standardized surface meshes, is a significant improvement over the prior state of the art, which has previously constrained such methods to only cortical regions (e.g. strictly gray or white matter surfaces).

Figure 3:
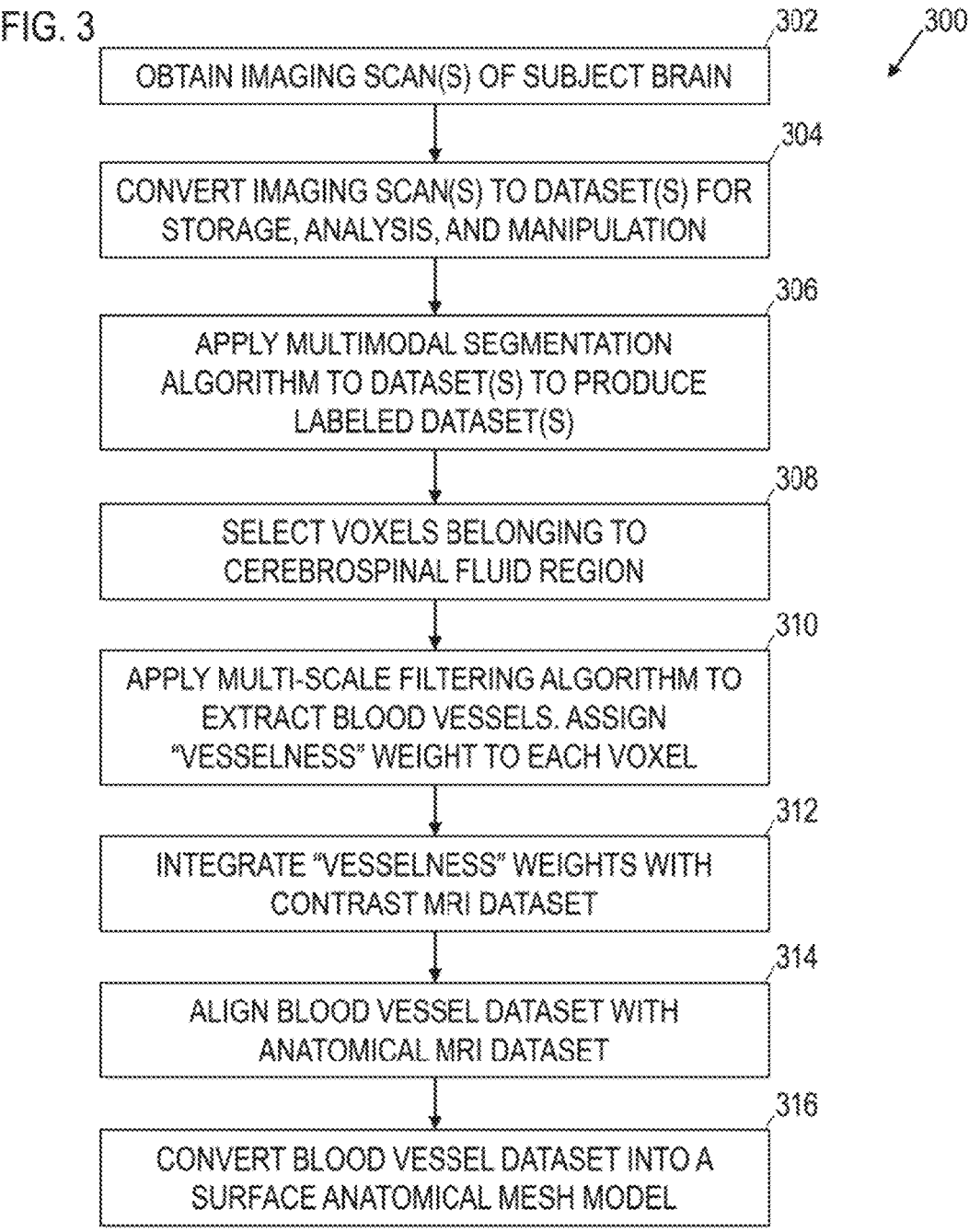
FIG. 3 shows a flow diagram for a method for automated segmentation of brain vasculature in accordance with the present disclosure.

FIG. 3 shows a flow diagram for a method 300 for automated segmentation of brain vasculature, and the generation of 2D/3D surface- and volume-based models in accordance with the present disclosure. Though depicted sequentially as a matter of convenience, at least some of the actions shown can be performed in a different order and/or performed in parallel. Additionally, some implementations may perform only some of the actions shown. Operations of the method 200 may be performed by a computing system as disclosed herein.

In block 302, one or more imaging scans of a subject's brain are obtained. The imaging scans include a contrast-weighted MRI scan (e.g. a T1-weighted MRI with contrast, which will be referred to as the Contrast MRI dataset).

In block 304, the imaging scans are converted from original imaging storage formats (e.g. DICOM) to 3D datasets as per the method 100. During conversion, the intensity values of the contrast MRI are variably up-scaled (e.g. 100×) to facilitate the differentiation between contrast enhanced structures (e.g., blood vessels) from their surroundings.

In block 306, a sequence-adaptive multimodal segmentation algorithm is used to generate a labelled dataset from the Contrast MRI, as per the method 100.

In block 308, the mask from the labeled dataset, generated as described in the method 100, for the Contrast MRI dataset is used to sub-select all voxels identified as belonging to the cerebrospinal fluid (CSF) region. The CSF mask (the sub-selected voxels) provides a novel improvement to the blood vessel segmentation algorithm, as the high-intensity voxels representing blood vessels are localized most commonly in the CSF, adjacent to the pial surface. This is especially true for those blood-vessels considered to confer the greatest risk for clinically significant hemorrhage (typically vessels with diameters ≥1.5 mm. Similar masks for gray and white matter labeled regions are also generated.

In block 310, a multi-scale filtering algorithm designed to enhance the tubular features in imaging data is used to extract blood vessels from adjacent voxels reflecting CSF or background noise. In general, the filtering algorithm utilizes a Hessian-based eigen-decomposition to derive eigen values and vectors at each pixel of the dataset at varying spatial scales to select tubular structures corresponding to blood vessels of differing diameters (see, for example: Frangi, Alejandro F., et al. Multiscale vessel enhancement filtering. Medical Image Computing and Computer-Assisted Intervention-MICCAI'98. Springer Berlin Heidelberg, 1998. 130-137). The software algorithm returns an output that has assigned to each voxel a weight of "vesselness", which range, for example, from 0 to 1, where higher weights representing voxels with more vessel-like features (e.g. tubular).

In block 312, information from the vesselness-weighted dataset is integrated with the Contrast MRI dataset to weight intensity value of the non-zero voxels by their relative "vesselness" weight and to penalize those voxels that overlap with white or gray matter.

In block 314, the blood vessel dataset is aligned to the Anatomical MRI dataset using the transformation matrix generated in block 306 (as described in the method 100).

In block 316, the blood vessel dataset is converted into a surface anatomical mesh model (as described for block 204 of the method 200) that can be visualized using varying levels of transparency and illumination.

Figure 4:
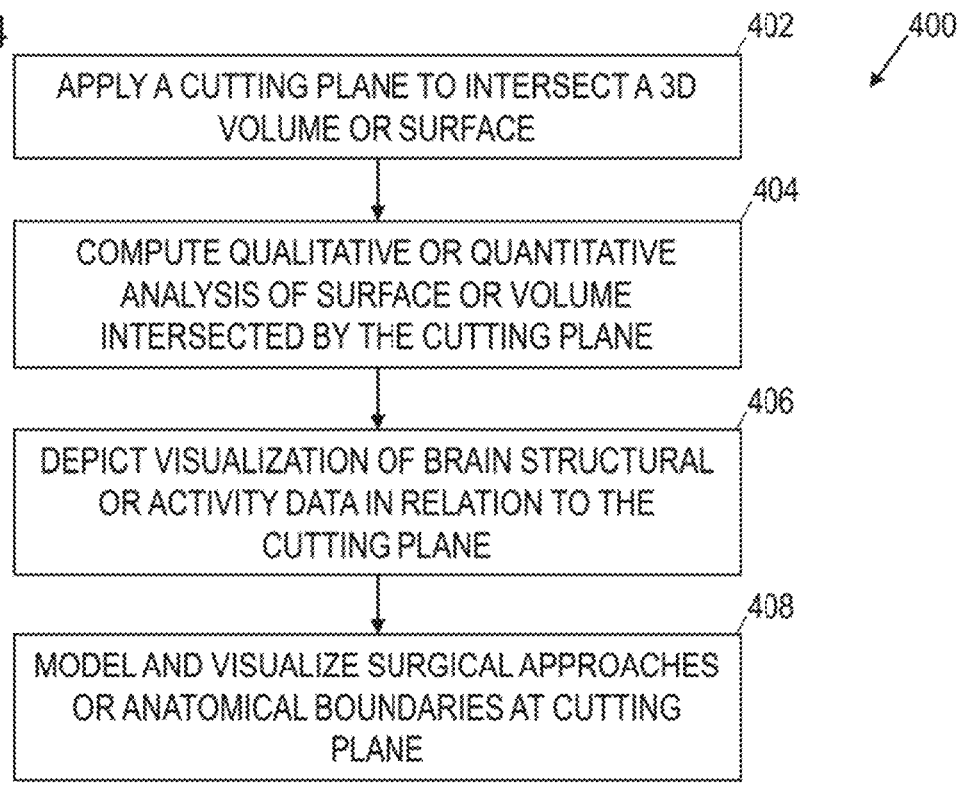
FIG. 4 shows a flow diagram for a method for visualizing underlying brain structures in accordance with the present disclosure.

FIG. 4 shows a flow diagram for a method 400 for visualizing underlying brain structures in accordance with the present disclosure. Though depicted sequentially as a matter of convenience, at least some of the actions shown can be performed in a different order and/or performed in parallel. Additionally, some implementations may perform only some of the actions shown. Operations of the method 400 may be performed by a computing system as disclosed herein.

In block 402, a cutting plane (e.g., a 2D cutting plane) in 3D space, in any user defined axis, intersects with a 3D volume or a surface. At the intersection of the cutting plane with a given surface mesh model or the 3D volume, all components of the mesh on either side of the cutting plane can be rendered selectively visible, invisible, or semi-transparent. On this plane any surface and/or volumetric (structural or functional) data can be simultaneously visualized. In general, the operations of block 402 may be performed by defining a cutting plane along one and/or more of the 2D anatomical imaging planes of the imaging dataset (exemplary embodiments of which include the coronal, sagittal, or axial plane of an MRI and/or CT scan). The intersection of the cutting plane and the imaging dataset may be defined along any arbitrary geometry (exemplary embodiments of which could include orthogonal and/or oblique angles), and the points along the intersection of these two planes identifies the voxels of the associated 3D volumetric imaging dataset that will be used for further display and/or analysis. These voxels may then be selectively visualized alongside the subject's 3D surface model. And the relationship of the coordinates of the voxel to the coordinates of the 3D surface models (e.g. at their points of intersection) may be further used to selectively render components of the surface model visible, invisible, or semi-transparent on either side of the cutting plane, or along the cutting plane itself. The coordinates of the voxels along the cutting plane may also be used to determine their distance from the implanted electrodes in the subject, which may then be used to compute and generate surface and/or volumetric data representations in relation to the cutting plane.

In block 402, when applied to extra- and intracranial anatomical meshes as defined in the methods 200 and/or 300, qualitative and quantitative analyses of the surface or volume intersected by the cutting plane may be computed, including but not restricted to computation of morphometric features such as curvatures, thickness, and area of cortical gray/white matter and/or subcortical structures, as well as the hippocampal and amygdala curvatures, thickness and areas. Further, the edges of the intersected surface and/or volume can be selectively raised or lowered to increase precision of visualization. In one exemplary embodiment, the intersection of the cutting plane with specific elements of the 3D surface may include a variety of cortical and/or subcortical surfaces layers, exemplary embodiments of which include the pial and/or white matter surfaces. For these exemplary embodiments, the intersection of the cutting plane with these surfaces will determine intervening gray matter between these two exemplary surfaces. The intervening gray matter may otherwise be referred to as the cortical ribbon. And by computing the distances between the points of the pial and white matter surfaces that lie along their intersection with the cutting plane (e.g., orthogonal distances between these two surfaces at their intersection with the cutting plane), the thickness of the cortical ribbon can be computed. By integrating the thickness across the length of the cortical ribbon, the area can be computed. In another exemplary embodiment, the curvature of the surfaces (e.g. the pial surface mesh) may be computed by drawing orthogonal lines outward from the faces of the surface mesh triangles to determine if these lines intersect the face of another mesh triangle. Such intersections occur when two triangular faces are pointed towards each other, as in the case of sulci. Using the angle and distance of such intersections, local topological features such as surface curvature and sulcal boundaries may then be determined.

In block 404, when applied to the extra- and intracranial anatomical meshes as defined in the methods 200 and/or 300, the visualization of brain structural data (including one or more of MRI, CT, PET, fMRI, DTI) and/or brain activity data (including one or more of EEG or MEG or brain stimulation) in relation to the cut planes of the various anatomical mesh models may be selectively depicted.

In block 406, when applied to the extra- and intracranial anatomical meshes as defined in the methods 200 and/or 300, users can make virtual cuts of arbitrary shape or geometry (e.g. a dome shaped surface or a surface that matches a craniotomy) by selecting a path along a surface and how deep within the surface to apply the cut, in which fashion a user can model and visualize surgical approaches or various anatomical boundaries for clinical evaluation and/or surgical planning or training and/or educational visualizations.

Figure 5:
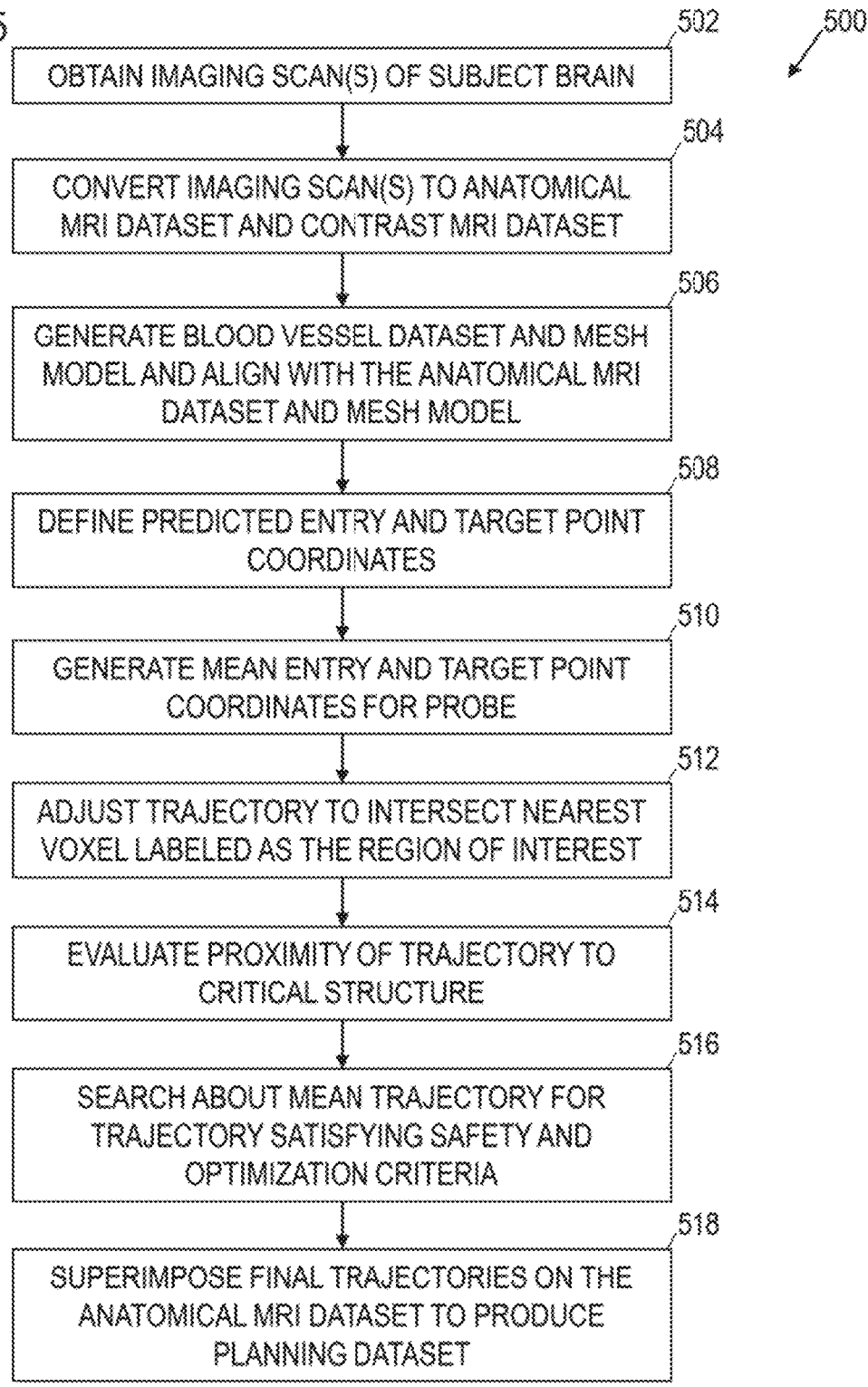
FIG. 5 shows a flow diagram for a method for automated planning of electrode or probe implantation in accordance with the present disclosure.

FIG. 5 shows a flow diagram for a method 500 for automated planning of electrode or probe implantation in accordance with the present disclosure. Though depicted sequentially as a matter of convenience, at least some of the actions shown can be performed in a different order and/or performed in parallel. Additionally, some implementations may perform only some of the actions shown. Operations of the method 500 may be performed by a computing system as disclosed herein.

The method 500 provides for precise and automated planning of electrode or penetrating probe implantation trajectories using a prior probability distribution derived from a previously implanted population to the anatomical target to be implanted or targeted. The prior probability distribution is generated using the entry and/or target coordinates of the trajectories from the previously implanted population, which have been aligned to a subject's brain using linear or non-linear deformation algorithms (or vice-versa). Further, the general implantation strategy is derived from clinical consideration of the likely anatomical region/s using a description of the clinico-electrical syndrome linking the subject's seizure semiology or other electro-clinical characterizations of epilepsy. In each case, the trajectory will have the additional goal of avoidance of critical structures (e.g. blood vessels) through the use of loss-functions and risk-metrics. Additionally, these trajectories may, in one embodiment, be solely created by a physician or surgeon, skilled in the art of stereotaxis, by defining entry and target points of interest.

In block 502, one or more imaging scans of a subject's brain are obtained. The imaging scans include a target anatomical MRI scan (e.g., a T1-weighted MRI without contrast) and a contrast-weighted scan (e.g. T1-weighted MRI with contrast).

In block 504, the imaging scans are converted from original imaging storage formats (e.g. DICOM) to datasets as per the method 100. The T1-weithed MRI without contrast is converted to a dataset referred to as the Anatomical MRI dataset, and the T1-weighted MRI with contrast is converted to a dataset referred to as the Contrast MRI dataset.

In block 506, a blood vessel dataset and mesh model are generated and co-registered to the Anatomical MRI dataset and its related mesh models as per the method 100.

In block 508, a predicted entry and target point coordinate in the current subject's own anatomical space is defined using target point and entry point coordinates curated from the population cohort of prior implanted subjects. Coordinates from the population were previously co-registered to a high-resolution template atlas. In one exemplary embodiment the template coordinate space could be the coordinates space defined as in standard co-ordinate space (e.g. Talairach space; Montreal Neurological Institute space). Co-registrations may be achieved using non-linear or linear/rigid/affine transformations, and computed in an inverse-consistent and symmetric fashion such that the template coordinates can be transformed to the patient's coordinate space in a topologically accurate fashion and the reverse transform can be applied following implantation of the current subject's electrodes, to further add to the population prior dataset.

In block 510, for each probe, the group of entry and target point coordinates for that probe are averaged to generate a mean target and entry point in subject's anatomical coordinate system, from which a mean trajectory is defined. For each probe, anatomical parcellations are further associated with the probe and can be used to further constrain the predicted trajectory in exemplary cases where the anatomical region of interest is small in volume, and/or in close proximity to other sensitive anatomical structures, and/or the variability in target coordinate spread from the prior population may be larger than the diameter of the structure. In this fashion, in one exemplary embodiment, anatomical parcellations and prior implanted trajectory distributions can be used to develop prior information to enable the implantation of the penetrating probe. In another exemplary embodiment, the anatomical target may be quite large (e.g. as in the cingulate gyrus, which extends in a C-shape from the anterior portions to the posterior aspects of the cranium) and in such circumstances, the target coordinates from the prior population may constrain the desired target location to the anterior, middle, or posterior aspect of the cingulum (exemplar trajectories here would be AC=anterior cingulate; MC=middle cingulate; PC=posterior cingulate), while the anatomical parcellations may further constrain the final target coordinate to remain within the boundaries of the cingulum, which is known to curve from inferior to superior and back down, as well as from anterior to posterior and back, along its route. In a further exemplary embodiment, the patient's seizure semiology might be used by a clinician who is skilled in the art to derive information about the likely specific anatomical region responsible for the epilepsy. This understanding can then be translated to inform the trajectory plan by constraining the trajectory to the anatomical parcellation of interest. In another embodiment, surgical trajectories may solely be manually created by an individual skilled in the art of stereotaxis, by defining entry and target points of interest, and optimizing these relative to blood vessels and other possible trajectories. Alternatively, they may be derived by some combination of derivation from the mean population-based trajectory combined with manual optimization.

In block 512, constraint to anatomical parcellations may be achieved by adjusting the trajectory so that it intersects with the nearest voxel with the label assigned from the anatomical region of interest, where distance is determined by computing Euclidean distance between the voxels of the probe trajectory and the labelled voxels in the anatomical parcellation of interest.

In block 514, the intersection of the trajectory with any critical structure, such as blood vessels is evaluated using a loss-function, by determining such trajectory intersections with 2D and/or 3D surface and/or volume regions labelled or identified as belonging to the critical structure, with penalization of trajectories for any such intersections. Further, the proximity of this trajectory to a critical structure such as a blood vessel is checked against user-determined constraints (e.g. >2 mm from the edge of blood vessel, or ≥4 mm from the center of an adjacent probe's trajectory).

Automated loss or optimization functions may also be incorporated in the trajectory planning, such that—in one exemplary embodiment—the total intracranial length is minimized while gray matter sampled is maximized to enable maximal potential of recording.

In block 516, beginning from initial trajectory estimated by the prior information (defined by the mean entry and target points across the population), the method 500 commences a local search surrounding this mean point until a trajectory as close as possible to the mean trajectory, that satisfies all safety and optimization criteria is identified. The search region is defined as a frustum with the diameter of each end defined in terms of standard deviation of the distribution of target and the center of each end defined by the mean entry and target coordinates from the group population.

In block 518, the final trajectories are superimposed on the Anatomical MRI dataset to generate a new planning dataset that can be exported in any fashion for use with other software or hardware systems to visualize the trajectory plans in relation to the subject's anatomy.

When used with the visualization techniques of the method 400, verification of an implantation plan of multiple stereotactic depth probes along oblique trajectories is aided by simultaneous visualization of a cortical mesh model of surface topology and deep anatomy revealed by structural magnetic resonance imaging, sliced along a plane colinear with the proposed trajectory. The slicing of the brain surface in any given plane enables the visualization of deep buried cortex in 3D and also enables rapid confirmation of the surgical plan by clinicians.

Integration of the planning operations of the method 500, with the anatomical visualization and analysis techniques of the methods 100-400, enable a clinician to identify critical extra cranial and intracranial structures (including but not limited to structures such as ventricles, white matter pathways, vessels and eloquent regions) and avoid unwanted iatrogenic outcomes that include but not limited to hemorrhage and/or visual, linguistic, cognitive, spatiotemporal, and/or sensorimotor deficits.

Incorporating the methods 100-500 with white-matter pathway analyses using deterministic or probabilistic tractography (derived from diffusion imaging) can further identify risks to pathways involved in crucial functions such as motor, sensory, auditory, or visual processes. In a specific indication—this approach may be applied to the reduction of visual deficits after laser interstitial thermal therapy of the hippocampus and/or amygdala for mesial temporal lobe epilepsy. 3D planning of the optimal trajectory for targeting the medial temporal lobe, combined with the visualization of pathways identified by diffusion imaging may be used to increase the therapeutic window of this technique.

Figure 6:
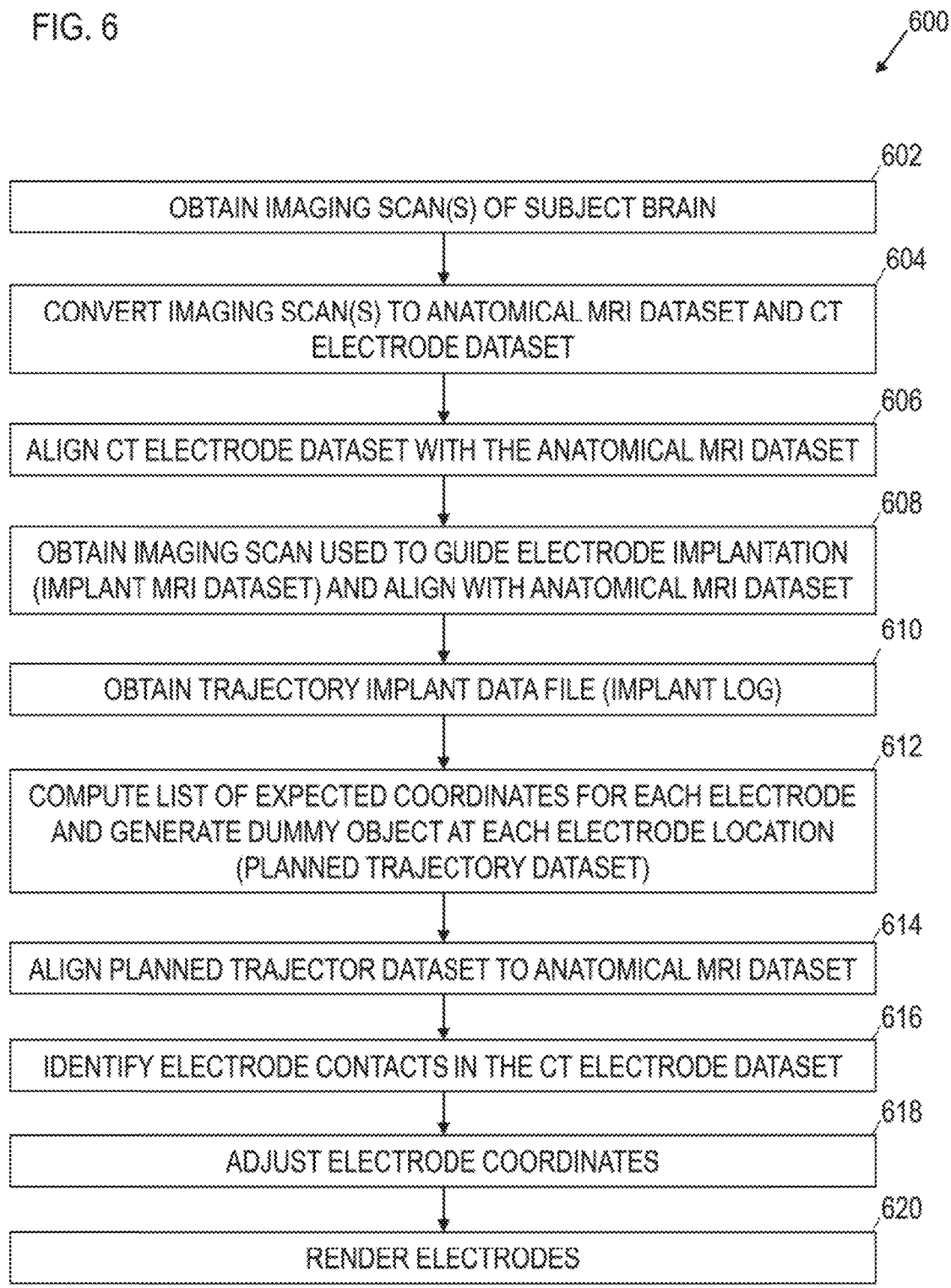
FIG. 6 shows a flow diagram for a method for automated localization, naming, and visualization of previously implanted electrodes or penetrating brain probes in accordance with the present disclosure.

FIG. 6 shows a flow diagram for a method 600 for automated localization, naming, and visualization of previously implanted electrodes or penetrating brain probes, combined with resolution of implanted structures in post-surgical imaging using a template-matching search algorithm and planned trajectories. Though depicted sequentially as a matter of convenience, at least some of the actions shown can be performed in a different order and/or performed in parallel. Additionally, some implementations may perform only some of the actions shown. Operations of the method 600 may be performed by a computing system as disclosed herein.

In block 602, one or more imaging scans of a subject's brain are obtained. The imaging scans include a target anatomical imaging scan (e.g. T1-weighted MRI without contrast) and a post-implantation CT imaging scan obtained after electrodes are implanted, to be used to localize each electrode's actual location.

In block 604, the imaging scans are converted from original imaging storage formats (e.g. DICOM) to datasets as per the method 100. The T1-weighted MRI without contrast is converted to a dataset referred to as the Anatomical MRI dataset, and the CT imaging scan is converted to a dataset referred to as the CT electrode dataset.

In block 606, both datasets are co-registered, and the CT Electrode dataset is aligned to the Anatomical MRI as per the method 100.

In block 608, a third imaging scan is obtained. The third imaging scan is actually used by the surgeon as the anatomical imaging dataset during surgery to guide electrode implantation (referred to herein as the Implant MRI dataset or imaging scan). In one exemplary embodiment, this scan may be a T1-weighted MRI with contrast enhancement, used to provide both high resolution anatomical detail and to reveal location of blood vessels during implantation planning. The Implant MRI imaging scan is imported, co-registered, and aligned to the Anatomical MRI as per the method 100.

In block 610, a trajectory implant data file (referred to herein as the implant log) is obtained. The implant log was created when the implantation was performed, an exemplary embodiment of which is a subject's implantation file generated by a robotic sEEG implantation system (e.g. the Zimmer ROSA™ robot), and another example is the stereotactic file created by navigation systems (e.g., BrainLab™ and Medtronic Stealth™). The implant log includes information regarding probe/trajectory names and/or the planned target and/or entry point coordinates and/or the probe trajectory vector defined in relation to the patient's coordinate space of the Implant MRI (as described in the method 500).

The method 500 may also include a security/manual verification feature whereby the user is manually required to enter the probe names, number of electrodes on each probe, and the number of electrodes to ignore from each probe (e.g. for electrodes in the anchor bolt, outside of the brain, or not included in the recording, etc.). The initial list of names and estimated electrodes per probe may be automatically obtained and provided to the user as a template by reading the aforementioned information directly from the implant log or its equivalent should it be available.

In block 612, the planned target and entry point coordinates provided for each probe from the implant log, along with numbers of electrodes in each probe as verified by the user, are used to compute an initial list of expected coordinates for each electrode. This computation is performed using the axis of the trajectory computed from the entry and target point coordinates, the distance between the entry and target point coordinates, and the spacing between electrodes. This information is used to generate "dummy" objects at the estimated locations of each electrode for each of the probe trajectories. An exemplary embodiment of such a "dummy" object may be a sphere that is centered around the coordinate with a given geometry that matches the electrode geometry (e.g. a cylinder). This new dataset (referred to herein as the planned trajectory dataset) has the same volume geometry and coordinate space as the implant MRI dataset.

In block 614, the planned trajectory dataset is aligned to the Anatomical MRI dataset using the transformation matrix generated by the alignment of the Implant MRI dataset to the Anatomical MRI dataset.

In block 616, Using the CT Electrode and Planned Trajectory datasets are co-registered to the subject's Anatomical MRI dataset using as per the method 100, and a binarization operation is performed on the CT Electrode dataset in which imaging voxels (e.g. possibly of 1 mm×1 mm×1 mm cube dimensions containing intensity information from the image, functioning as a 3D pixel equivalent) below an automatically determined threshold level are zeroed out. A 3D clustering algorithm is applied to the remaining voxels to identify voxels with high intensity signal (sometimes referred to as a metallic artifact) of the electrode contacts on the CT scan. An exemplary embodiment of the 3D clustering algorithm could be the standard clustering commands provided by the underlying neuroimaging analysis software used. An iterative search is performed by adjusting threshold value until the resulting numbers of clusters are similar to the expected number of electrodes. The coordinates of these clusters are iteratively compared to the coordinates of the spherical "dummy" electrodes generated for the Planned Trajectory datasets. Using line-distance in 3D space and center of mass for distance metrics, the clusters from the CT Electrode dataset and the trajectory paths and sphere object coordinates from the Planned Trajectory datasets are iteratively searched and optimized until all expected electrodes are identified and localized.

In block 618, the clustering algorithm combined with the trajectory path information and the number of electrodes expected, as provided by the input log and represented in the planned trajectory dataset, are used to adjust the final locations of the electrode coordinates. Final coordinate locations that best match the imaging data (e.g. cluster location), and the physical constraints of the expected trajectory (location along a specific line separated by a specific distance from adjacent electrodes on the same path) are thus derived.

In block 620, after all electrode coordinates are identified, 2D and/or 3D models of these electrodes are rendered for visualization, with appropriate electrode names and numbering schemes assigned. Electrodes are visualized using displayable objects, (e.g. cylinders or discs), that reflect the size, spacing and dimensions of each actual electrode. Having been co-registered to the anatomy MRI dataset, these electrodes can be visualized in relation to the 2D and/or 3D surface- and volume-based representations of the relevant extracranial and intracranial structures generated by the methods 200 and/or 300.

Displayable electrode objects may be individually manipulated (e.g. colored, annotated, numbered, visualized using different shapes or representations, turned on or off). They can be rendered transparent, translucent, or invisible along with any functional data (EEG) collected by the electrodes.

The methods and techniques described herein can be used in conjunction with other methods for the surface-based representation of recorded intracranial EEG or other general functional activation or general neural correlate measured using implanted electrodes and/or penetrating probes and/or imaging modalities. The method disclosed herein for surface-based representations can be applied not only to display the representation upon cortical structures but also the anatomical meshes generated for the hippocampus, amygdala, and/or other general subcortical or brain structures. Such methods are disclosed in U.S. Pat. No. 10,149,618.

Using the methods disclosed herein, data representations of interest can be constrained to specific electrodes and exported to a new dataset by superimposing the intensity values of the voxels of interest upon the Anatomical MRI dataset to generate a new Surface- or Volume-Activation dataset. In surface-based datasets, the activations are assigned to surface-nodes using geodesic spread functions as described in prior publications (Kadipasaoglu C M, Baboyan V G, Conner C R, Chen G, Saad Z S, Tandon N. Surface-based mixed effects multilevel analysis of grouped human electrocorticography. Neuroimage. 2014 Nov. 1; 101:215-24. doi: 10.1016/j.neuroimage.2014.07.006. Epub 2014 Jul. 12. PMID: 25019677). In volume-based datasets, the activations are constrained to the voxels that are located within the boundary between the pial and white matter surface layers (the cortical ribbon) underlying the electrodes of interest (Christopher R. Conner, Gang Chen, Thomas A. Pieters, Nitin Tandon, Category Specific Spatial Dissociations of Parallel Processes Underlying Visual Naming, Cerebral Cortex, Volume 24, Issue 10, October 2014, Pages 2741-2750, https://doi.org/10.1093/cercor/bht130). These datasets can be exported to disc in any fashion for use with other software or hardware systems to visualize these activations in relation to the subject's anatomy.

Figure 7:
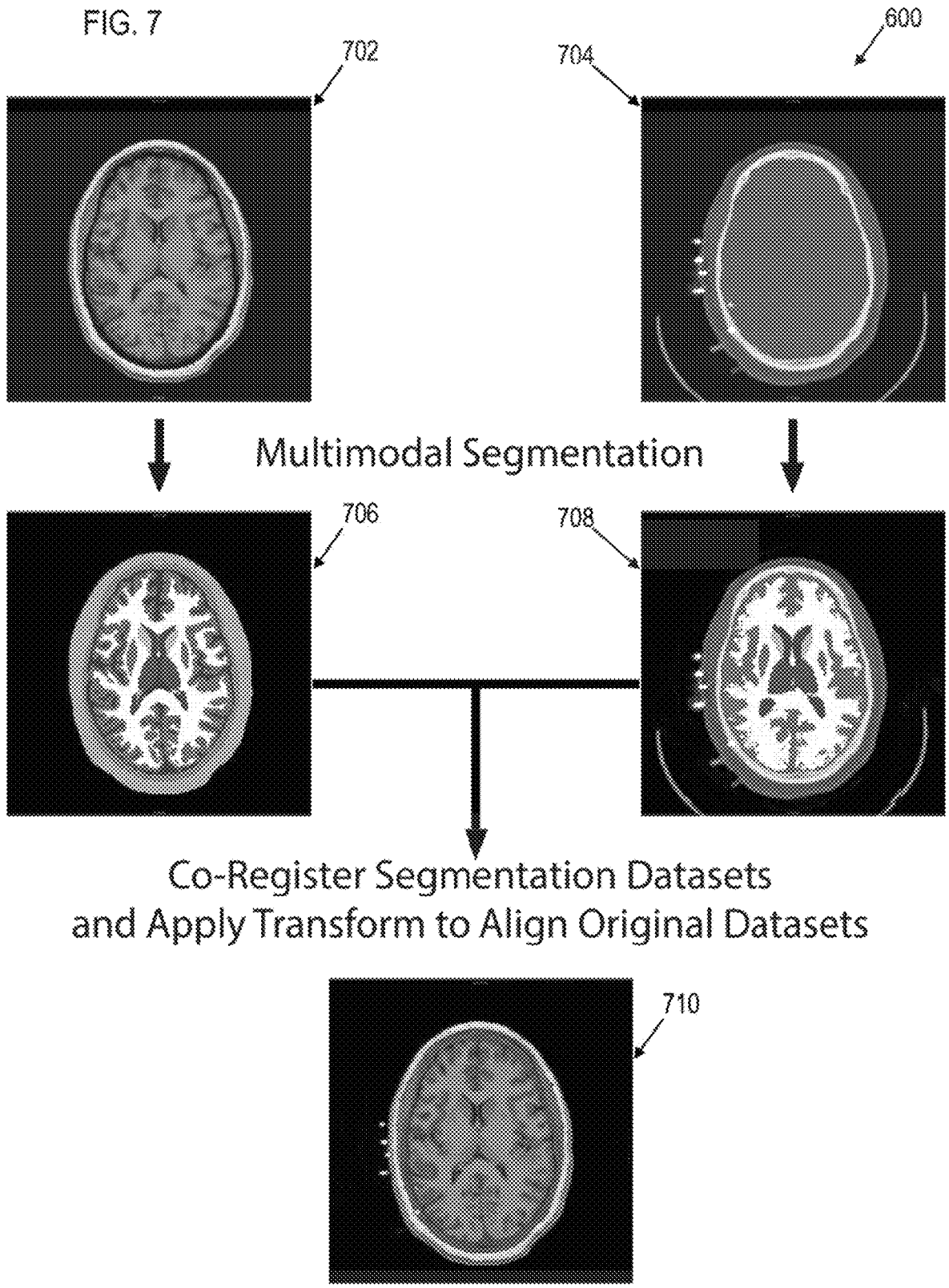
FIG. 7 shows a pictorial representation of co-registration of different neuroimaging modalities performed on a single subject in accordance with the present disclosure.

FIG. 7 shows a pictorial representation of co-registration of different neuroimaging modalities performed on a single subject in accordance with the present disclosure. In FIG. 7, sequence adaptive segmentation is applied to the dataset 702 to produce the labeled dataset 706, and sequence-adaptive segmentation is applied to the dataset 704 to produce the labeled dataset 708. The labeled datasets 706 and 708 are co-registered and a transformation matrix produced by the co-registration is applied to align the labeled datasets 706 and 708 as shown in dataset 710.

FIG. 8 shows a pictorial representation depicting a generation of 2D/3D surface models of the hippocampus as well as the thalamus in accordance with the present disclosure. FIG. 8A is an exemplary illustration of an anatomical mesh model of the right hippocampus generated from the segmentation of a 3D volumetric dataset of a subjects anatomical T1 MRI shown in FIG. 8B.

FIGS. 8B and 8C depict exemplary illustrations of 2D/3D surface mesh models of the left hippocamps and amygdala in a subject, which are visualized concurrently with the same subject's right cerebral hemisphere following an anatomical atlas-based parcellation. In FIG. 8C, the surface models are visualized as distinct structures. The left cortical hemisphere has been rendered transparent independently of the right, to allow for visualization of the left hippocampus and amygdala. In FIG. 8D, the parcellated right cortical hemisphere is rendered semi-transparent such that the solid-state rendering of the underlying right hippocampus and amygdala can be visualized.

FIGS. 8E and 8F illustrate an exemplary surface-based mesh model of a subject's left thalamus and its nuclei generated using parcellations derived from a microscopic stereotactic atlas. In FIG. 8E, the surface model is view in isolation. In FIG. 8F, the same model is viewed in relation to the three principle planes of the subject's original anatomical T1 MRI.

Figure 9A:
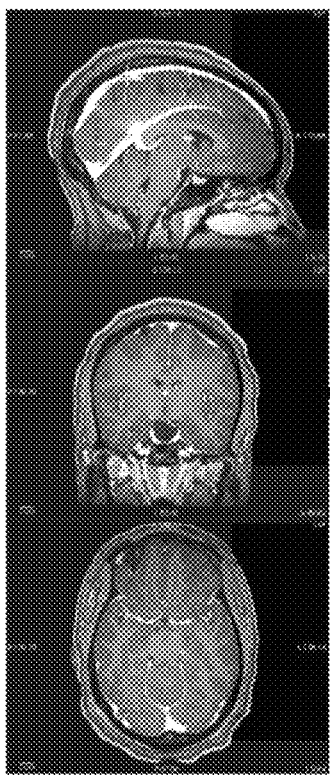
FIGS. 9A-9D show example steps for segmentation of human cerebrovasculature in accordance with the present disclosure.
Figure 9B:
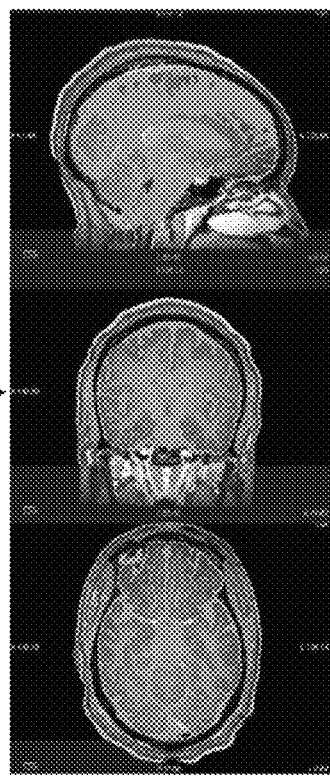
Figure 9C:
Figure 9D:
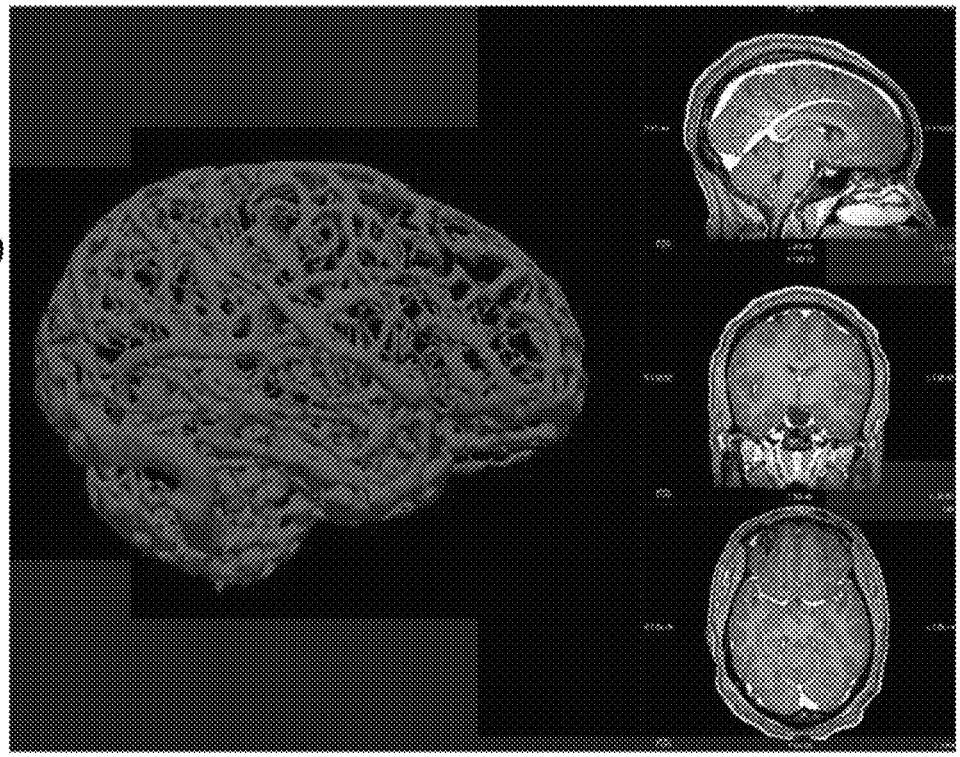

FIGS. 9A-9D show example steps for segmentation of human cerebrovasculature in accordance with the present disclosure. FIGS. 9A-9C depict the original imaging dataset (FIG. 9A, an exemplary embodiment of which here is a T1 MRI with contrast) that is subsequently masked by the cerebrospinal fluid segmentation volume (FIG. 9B) and then processed using a multi-scale Hessian based filtering algorithm to accurately segment the blood vessel voxels (FIG. 9C). FIG. 9D depicts the resulting vascular 3D surface model generated using the segmented blood vessel volume (right) as well as the overlay of the surface cerebrovascular model (outlined) over the three principal planes of the original contrasted T1 MRI dataset, demonstrating a comprehensive segmentation of the subject's vasculature.

Figure 10A:
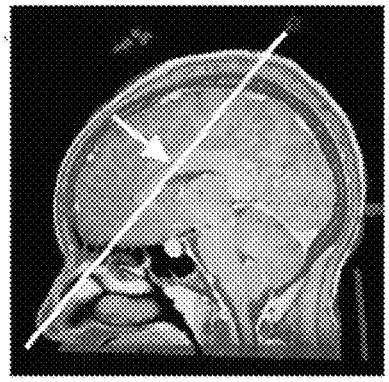
FIGS. 10A-10N and 10P-10W show use of a cutting plane to intersect with surface and volume models at arbitrary angles to optimize the visualization of cortical and subcortical structural and/or functional representations in accordance with the present disclosure.
Figure 10B:
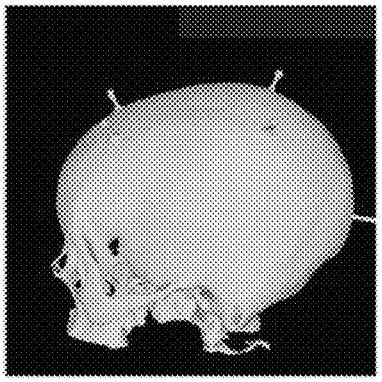
Figure 10C:
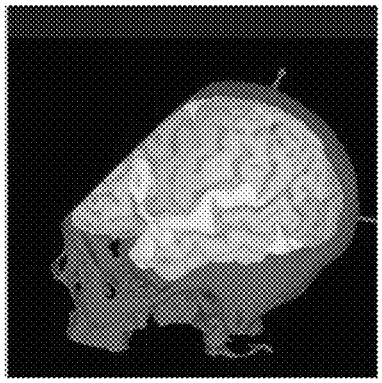

FIGS. 10A-10N and 10P-10W show a pictorial representation of using a 2D cutting plane ("slicer") to intersect with 2D and/or 3D surface and volume models at arbitrary angles to optimize the visualization of cortical and subcortical structural and/or functional representations. FIGS. 10A-10C depict a cutting plane viewed on a 2D sagittal plane view of a subject's anatomical T1-weighted MRI overlaid with CT skull shown in FIG. 10A. The 3D surface model of the subject's intact skull is shown in FIG. 10B, and the skull following application of the cutting plane is shown in FIG. 10C. The skull is rendered partially transparent to visualize the underlying parcellated cortical surface model with the same cutting plane applied.

Figure 10D:
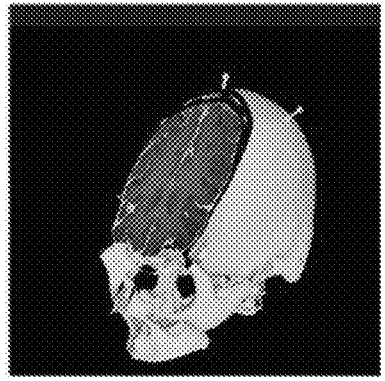
Figure 10E:
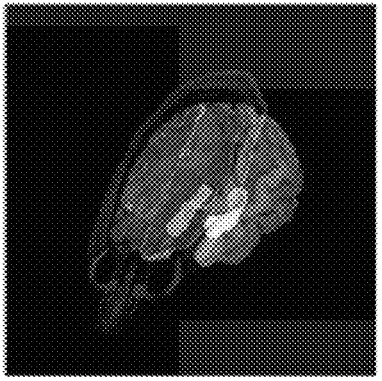
Figure 10F:
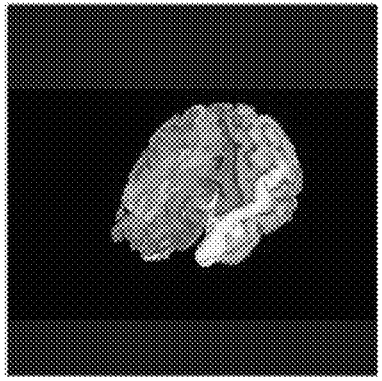

FIGS. 10D-10F show rotated views of the same subject skull and underlying parcellated cortical surface model. Note that the cutting plane may be rendered opaque and constricted within the boundaries of the 3D surface models, to display the associated 2D MRI planar images (FIG. 10D). Alternatively, the cutting plane may be rendered semi-transparent and/or extend the 2D MRI plane views beyond the boundaries of the underlying surface models (FIG. 10E). Finally, the cutting plane may be rendered invisible, and the underlying plane of the surface model rendered transparent, such that deep anatomical structures may be visualized (FIG. 10F).

Figure 10G:
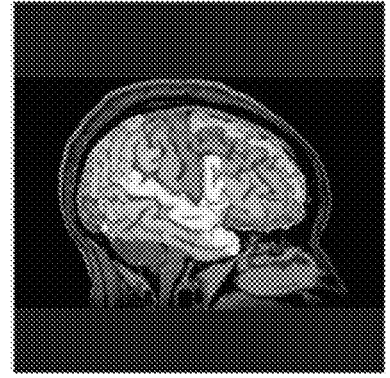
Figure 10H:
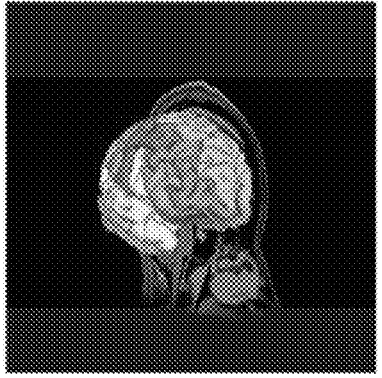
Figure 10I:
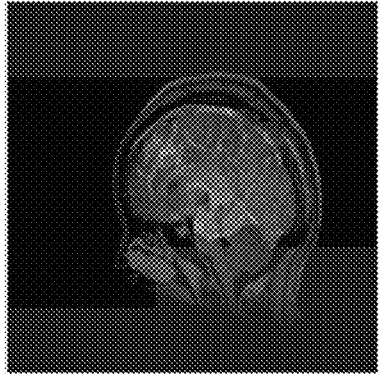

FIGS. 10G, 10H, and 10I show sagittal views of the 2D cutting plane and associated 3D parcellated cortical surface model at various rotated angles. In FIG. 10I, the edges of the cortical model are extended slightly beyond the boundaries of the cutting plane, with gyral and sulcal boundaries selectively enhanced to more precisely visualize underlying anatomical features.

Figure 10J:
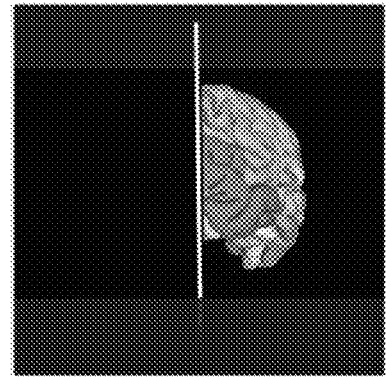
Figure 10K:
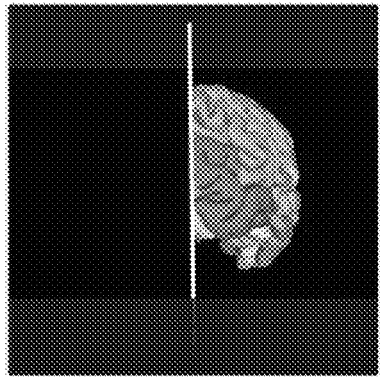
Figure 10L:
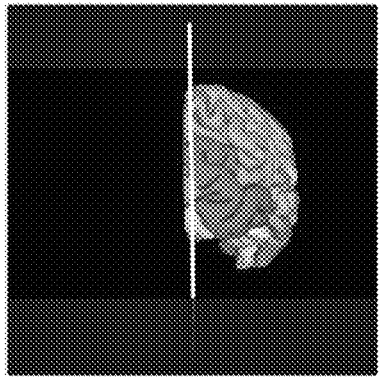

FIGS. 10J-10L show three views of the same 2D sagittal cutting plane and 3D cortical surface model shown in FIGS. 10G-10I, with the edges of the model retracted from the cutting plane (FIG. 10J), flush with the plane (FIG. 10K), and extended slightly beyond the plane (FIG. 10L).

Figure 10M:
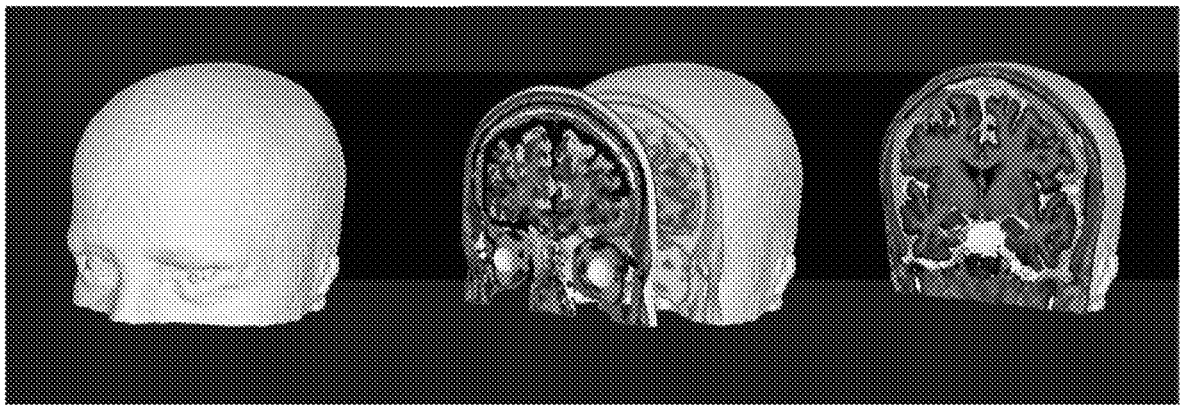
Figure 10N:
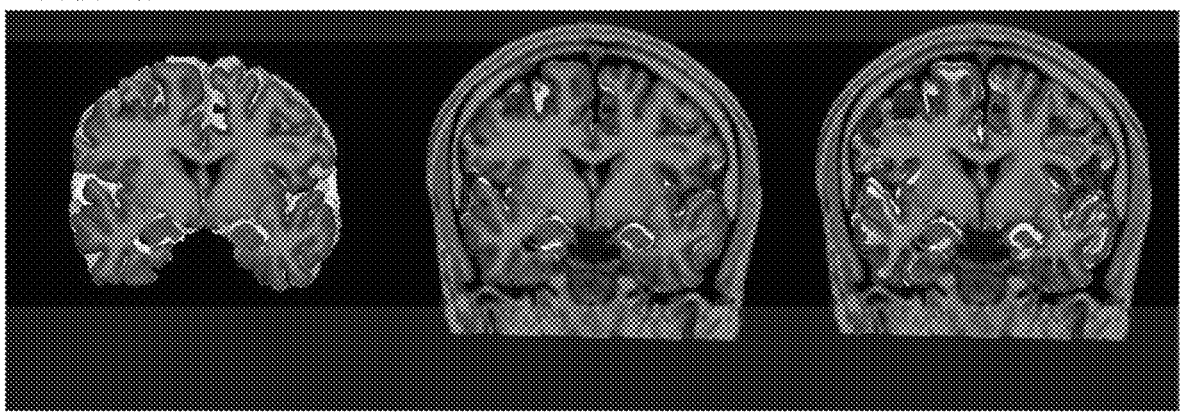
Figure 10P:
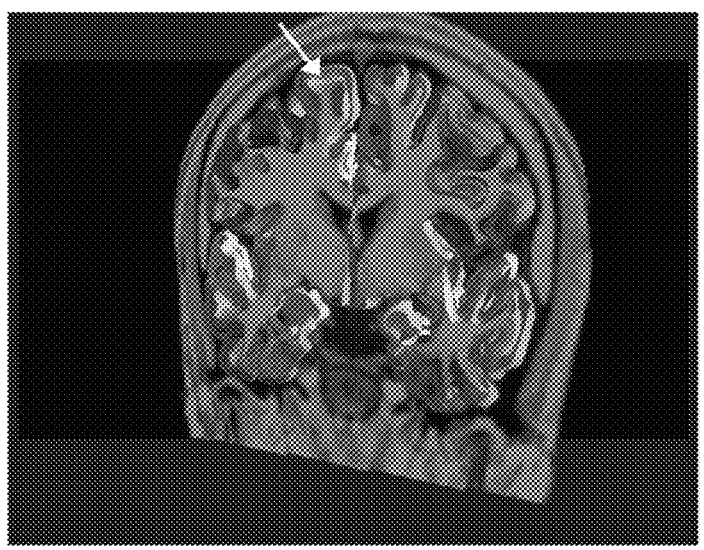
Figures 10Q, 10R, 10S, 10T, 10U, 10V, 10W:
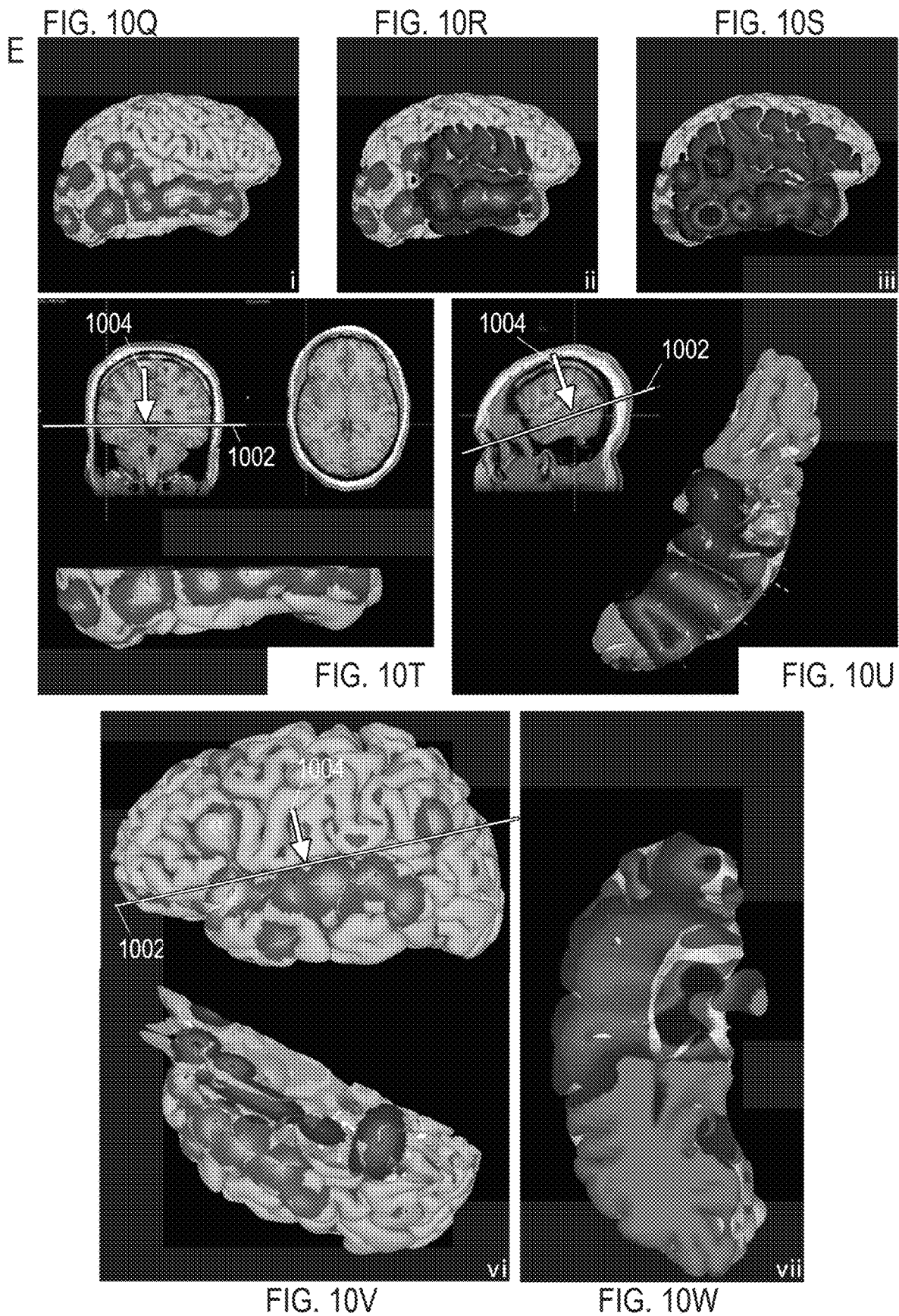

FIGS. 10M, 10N, and 10P show three views of a 2D coronal cutting plane and the 3D skin and parcellated cortical surface model. The intact skin model is intersected by the cutting plane, and the remaining component of the skin and parcellated cortical model are visualized (FIG. 10M). The parcellated cortical model is shown in isolation in FIG. 10N and in reference to the cutting plane, with the edges slightly extended beyond the plane, and then again in a third view, but in this view the edges are constrained to just the gray matter and white matter boundaries, such that the extension of the gray and white matter boundary edges beyond the cutting plane will isolate the intervening cortical ribbon. In FIG. 10P, an enlarged and slightly rotated view of the third image from FIG. 10N is depicted, with a white arrow indicating an exemplary region of the aforementioned cortical ribbon contained between the edges of the gray and white matter boundaries (FIG. 10P).

Figure 11G:
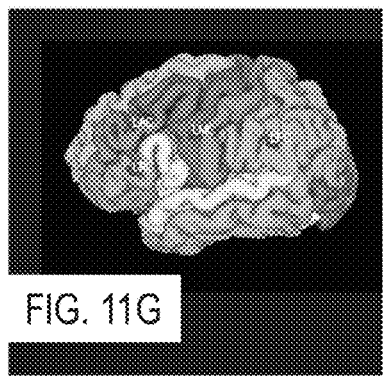

FIGS. 10Q-10W show cortex with simultaneous representation of surface and deep anatomical structures along with cortical activity represented as a color scale, via a slice along a plane colinear with a depth trajectory. The visualization of brain structural data (including one or more of MRI, CT, PET, fMRI, DTI) and/or brain activity data (including one or more of EEG or MEG or brain stimulation) in relation to the cut planes of the various anatomical mesh models may be selectively depicted to optimize visualization of functional activation in neocortical (FIGS. 10Q, 10R, 10S, 10T, and 10U) and/or hippocampal and amygdala (FIGS. 10V and 10W) and/or subcortical or other brain regions. Cutting planes and the associated viewpoint from which the relevant surfaces are visualized (FIGS. 10T-10V) are depicted by the line 1002 and arrow 1004, respectively FIGS. 11A-11H, 11J-11N, and 11P-11R show a pictorial representation of population-derived anatomical targeting for electrode or penetrating probe implantation, which incorporate priors derived using probability distributions from previously implanted populations and/or anatomical atlas-based parcellations and segmentations. FIGS. 11A-11D. depicts a grouped representation of trajectories into the brain from 130 patients implanted with 2600 electrodes to probe epilepsy, which have been co-registered and aligned to a common brain space and color coded by entry and target points (FIG. 11A). Electrodes may be further color-coded based on standard regional nomenclature applied to them, indicating similar entry and target points for specific cortical or subcortical foci across individuals, an exemplary embodiment of which is depicted for the right amygdala and hippocampus in a single subject (FIG. 11B). Using the information of prior trajectories from this population, a new trajectory may be derived for any specific brain region for a new individual (not one of the prior 130). An exemplary illustration of the analysis is provided for a single subject's right anterior hippocampus (RAH), where the new trajectory is depicted as the elongated cylinder, while the population prior trajectories are depicted either using each individual probe (FIG. 11C, shorter cylinders) or by visualizing the mean and variance of this population (FIG. 11D), which is depicted in this exemplary illustration with a frusta using the mean and 1.5× the standard deviation of entry and target point coordinates.

FIG. 11E depicts the integration of the oblique cutting plane, the detailed cerebrovascular and parcellated anatomical mesh models, and the trajectory planning algorithm to generate automated implantation trajectory plans for 12 different brain probes (e.g. sEEG probes). The automated algorithm ensures adherence to multiple safety constraints, exemplary embodiments of which may be a minimum distance from adjacent vessels along the trajectory as well from adjacent probes. The panel 11E-2 depicts an exemplary illustration of manual trajectory optimization in which two cylinders are visualized, representing the original (I.e. automatically-derived) and manually-adjusted trajectories for a right anterior hippocampal (RAH) probe.

FIG. 11F depicts a similar population-level derived plan for laser-interstitial thermal therapy of the amygdala and/or hippocampus for mesial temporal lobe epilepsy. Visualized are optimal new trajectories for a new subject, with the population-derived predicted ablation volumes expected for the given trajectories.

Figure 11H:
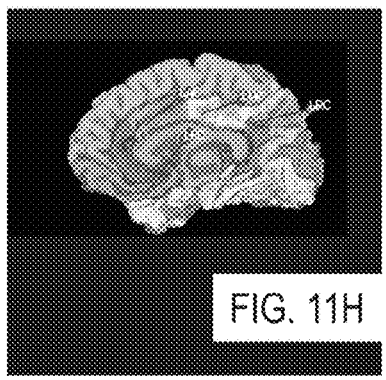
Figure 11J:
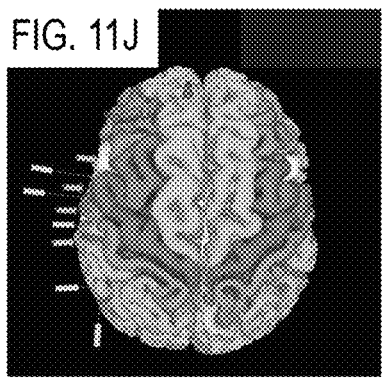

FIGS. 11G and 11H depict exemplary illustrations of new trajectories derived from the population data of prior implanted trajectories for multiple regions in the left cingulate gyrus, including the left rostral cingulate (LRC), anterior cingulate (LAC), medial cingulate (LMC) and posterior cingulate (LPC) regions. These illustrations include a lateral view highlighting the entry points (FIG. 11G) and a medial view depicting the proposed trajectories labeled by the aforementioned target brain regions, in which the left hemisphere has been rendered fully transparent such that the cingulate gyrus of the right hemisphere is visible (and may be used as a visual reference for the contra-lateral target brain regions), and in which the proposed trajectories have been depicted with their associated frusta (derived from the population) rendered as a semi-transparent overlay (FIG. 11H).

Figure 11K:
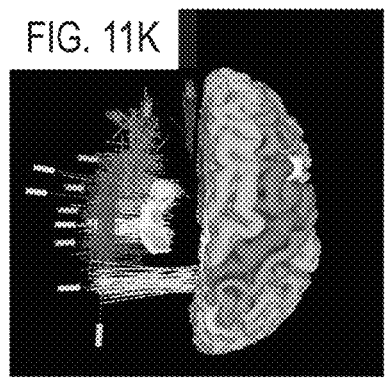
Figure 11L:
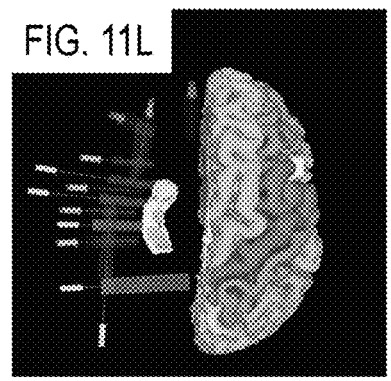
Figure 11M:
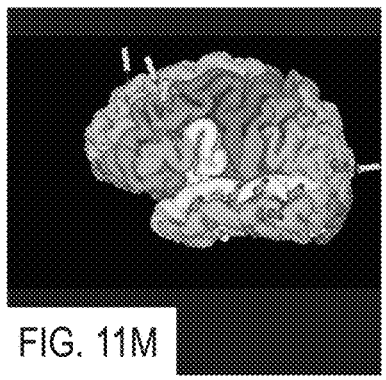
Figure 11N:
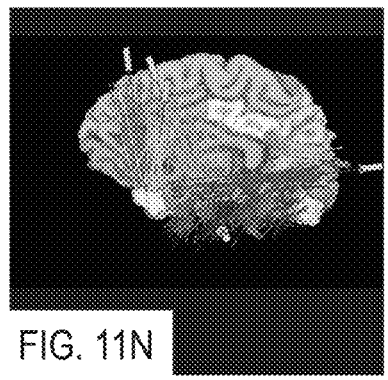
Figure 11P:
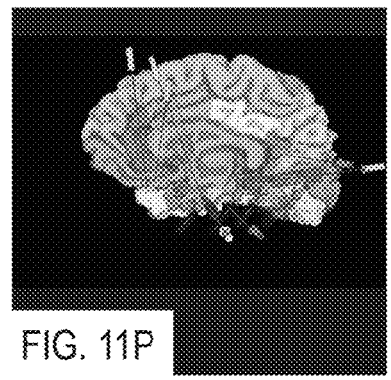
Figure 11Q:
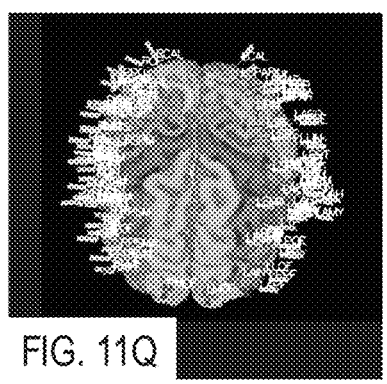
Figure 11R:
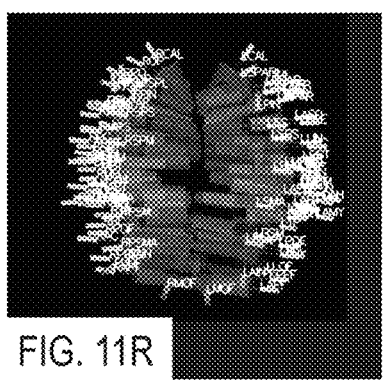

FIGS. 11J-11N and 11P depict exemplary illustrations of another subset of exemplary proposed trajectories that may be desired for a subject undergoing stereoencephalography evaluation for refractory epilepsy, using both superior (FIGS. 11J-11L) and lateral views of the 3D cortical surface model (11M-11N and 11P), in which the left hemisphere is rendered opaque (11J and 11M) or fully transparent (11K-11L, 11N, and 11P). The middle illustrations depict the population data of prior implanted trajectories used for the generation of their respective new trajectory, using cylinders color-coded by target brain region to visualize each of the prior implanted probes overlaid together with their respective new trajectory (FIGS. 11K and 11N). The mean and 1.5× the standard deviation from the distribution of coordinates of the population of prior implanted trajectories are used to generate the aforementioned frusta, which are depicted as semi-transparent overlays with their respective trajectories in the right-most illustrations (11L and 11P). The bottom row depicts an exemplary summary illustration of all trajectories from the population data of prior implantations, which are visualized with their respective frusta on a single exemplary subject's 3D cortical surface model that has been rendered both opaque and completely transparent (11Q and 11R, respectively).

FIG. 12A-12E depicts a pictorial representation of automated electrode localization and labelling, which incorporates the implantation trajectory log from a robotic sEEG implantation system to constrain and inform the electrode search algorithm and provide probe names and numbers of associated electrodes. The initial clustering algorithm applied to the post-implantation CT Electrode dataset is depicted in 12A, demonstrating how increasing intensity thresholds to zero out voxels with intensities below the threshold may be used to identify clusters of high-intensity voxels representing artifact from electrode contacts in the CT scanner. The trajectory implantation log from the robotic implantation system may also be used to further inform the electrode search by constraining the search space of the algorithm to more efficiently separate signal relating to electrode artifact from noise (FIG. 12B), and also ensure final electrode coordinates are spaced and aligned in a fashion consistent with the actual implantation as defined by the spherical dummy electrodes (FIG. 12C).

FIG. 12D depicts a cutting plane applied at an oblique angle to a subject's skull model to visualize the implanted electrodes in relation to the subjects right hippocampal and amygdala surface models. In this exemplary embodiment, each electrode is rendered as a cylinder with inter-electrode spacing and dimensions dictated by the implantation trajectory log and physical dimensions of the actual electrode. Probes and their respective electrodes are color-coded by probe name. A more zoomed view of the same subject's right hippocampus and amygdala is depicted in FIG. 12E with a subset of the implanted probes visualized as displayable objects and color-coded by their probe name, which is also annotated in white. The trajectories from the trajectory implantation log are also depicted here, though this time as semi-transparent cylinders with smaller dimensions and spacings to differentiate themselves from the true electrode locations. As can be seen by the highlighted electrode with the overlying crosshair, the final electrode coordinates do not always perfectly correspond to the planned trajectory, as the probes may be deflected during implantation. The highlighted electrode coordinate corresponds to the coordinates of the crosshairs in the adjacent 2D coronal and sagittal planar images of the same subject's pre-implantation MRI overlaid by the post-implantation CT.

Figure 13:
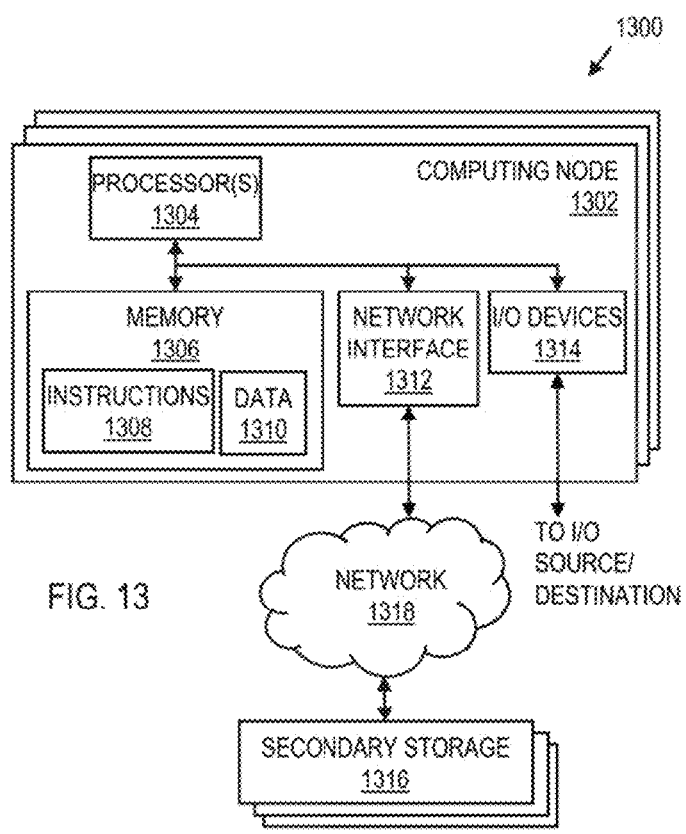
FIG. 13 shows a block diagram for a computing system suitable for implementation of the methods disclosed herein.

FIG. 13 shows a block diagram for a computing system 1300 suitable for implementation of the methods disclosed herein (e.g., the methods 100, 200, 300, 400, 500, and/or 600. The computing system 1300 includes one or more computing nodes 1302 and secondary storage 1316 that are communicatively coupled (e.g., via the network 1318). One or more of the computing nodes 1302 and associated secondary storage 1316 may be applied to perform the operations of the methods described herein.

Each computing node 1302 includes one or more processors 1304 coupled to memory 1306, a network interface 1312, and the I/O devices 1314. In various embodiments, a computing node 1302 may be a uniprocessor system including one processor 1304, or a multiprocessor system including several processors 1304 (e.g., two, four, eight, or another suitable number). Processors 1304 may be any suitable processor capable of executing instructions. For example, in various embodiments, processors 1304 may be general-purpose or embedded microprocessors, graphics processing units (GPUs), or digital signal processors (DSPs) implementing any of a variety of instruction set architectures (ISAs). In multiprocessor systems, each of the processors 1304 may commonly, but not necessarily, implement the same ISA.

The memory 1306 may include a non-transitory, computer-readable storage medium configured to store program instructions 1308 and/or data 1310 accessible by processor(s) 1304. The memory 1306 may be implemented using any suitable memory technology, such as static random-access memory (SRAM), synchronous dynamic RAM (SDRAM), nonvolatile/Flash-type memory, or any other type of memory. Program instructions 1308 and data 1310 implementing the functionality disclosed herein are stored within memory 1306. For example, instructions 1308 may include instructions that when executed by processor(s) 1304 implement one or more of the methods disclosed herein.

Secondary storage 1316 may include volatile or non-volatile storage and storage devices for storing information such as program instructions and/or data as described herein for implementing the methods described herein. The secondary storage 1316 may include various types of computer-readable media accessible by the computing node 1302 via the network interface 1312. A computer-readable medium may include storage media or memory media such as semiconductor storage, magnetic or optical media, e.g., disk or CD/DVD-ROM, or other storage technologies.

The network interface 1312 includes circuitry configured to allow data to be exchanged between the computing node 1302 and/or other devices coupled to the network 1318. For example, the network interface 1312 may be configured to allow data to be exchanged between a first instance of the computing system 1300 and a second instance of the computing system 1300. The network interface 1312 may support communication via wired or wireless data networks.

The I/O devices 1314 allow the computing node 1302 to communicate with various input/output devices such as one or more display terminals, keyboards, keypads, touchpads, scanning devices, voice or optical recognition devices, or any other devices suitable for entering or retrieving data by one or more computing nodes 1302. Multiple input/output devices may be present in a computing system 1300.

The computing system 1300 is merely illustrative and is not intended to limit the scope of embodiments. In particular, the computing system 1300 may include any combination of hardware or software that can perform the functions disclosed herein. Computing node 1302 may also be connected to other devices that are not illustrated, in some embodiments. In addition, the functionality provided by the illustrated components may in some embodiments be combined in fewer components or distributed in additional components. Similarly, in some embodiments the functionality of some of the illustrated components may not be provided and/or other additional functionality may be available.

The above discussion is meant to be illustrative of the principles and various embodiments of the present invention. Numerous variations and modifications will become apparent to those skilled in the art once the above disclosure is fully appreciated. It is intended that the following claims be interpreted to embrace all such variations and modifications.

What is claimed is:

1. A method, comprising:
    obtaining a first imaging scan and a second imaging scan of a single subject brain;
    converting the first imaging scan to a first dataset, and the second imaging scan to a second dataset;
    applying an adaptive segmentation algorithm to the first dataset and the second dataset, wherein the adaptive segmentation algorithm performs automatic intensity-based tissue classification to generate a first labeled dataset and a second labeled dataset;
    automatically co-registering the first labeled dataset and the second labeled dataset to each other to generate a transformation matrix based on the first labeled dataset and the second labeled dataset; and
    applying the transformation matrix to align the first dataset and the second dataset.

2. The method of claim 1, wherein:
    the single subject brain comprises a cerebrospinal fluid region;
    the first imaging scan is a contrast weighted scan and the first dataset is a contrast weighted dataset; and
    the method further comprises:
    selecting voxels of the first dataset identified as belonging to the cerebrospinal fluid region;
    applying a filtering algorithm to identify voxels of the first dataset representing blood vessels and assign a vesselness weight value to each voxel;
        integrating the vesselness weight values into the first dataset; and
    after aligning the first dataset and the second dataset, converting the first dataset to a surface anatomical mesh model.

3. The method of claim 1, wherein the adaptive segmentation algorithm assigns a numeric label value to each voxel of the first dataset or the second dataset.

4. The method of claim 1 wherein the method further comprises:
    defining predicted target point coordinates and entry point coordinates for a probe based on target point coordinates and entry point coordinates of previously implanted probes or by user defined target and entry points;
    defining a trajectory for the probe based on a mean target coordinates and mean entry point coordinates;
    adjusting the trajectory to intersect with a nearest voxel assigned a label of an anatomical region of interest;
    checking proximity of the trajectory to critical structures based on user defined constraints and/or user defined modification of the trajectory to satisfy the user defined constraints; and
    superimposing the trajectory on the second data set to form a planning dataset.

5. The method of claim 1, wherein:
the first imaging scan is an anatomical scan, the second imaging scan is a post-implantation imaging scan, the first dataset is an anatomical dataset, and the second dataset is a post-implantation imaging dataset; and
the method further comprises:
obtaining a third imaging scan used to guide electrode implantation during surgery;
converting the third imaging scan to a third dataset;
aligning a third dataset with the first dataset;
obtaining a trajectory implant data file created during the electrode implantation;
generating a planned trajectory dataset, based on trajectory implant data file, that includes dummy objects disposed at locations of electrode geometry;
aligning the planned trajectory dataset to the imaging dataset; and
automatically identifying and labelling electrodes in an electrode dataset based on the dummy objects of the trajectory implant data file.

6. A non-transitory computer-readable medium encoded with instructions that are executable by one or more processors to:
obtain a first imaging scan and a second imaging scan of a single subject brain;
convert the first imaging scan to a first dataset, and the second imaging scan to a second dataset;
apply an adaptive segmentation algorithm to the first dataset and the second dataset, wherein the adaptive segmentation algorithm performs automatic intensity-based tissue classification to generate a first labelled dataset and a second labeled dataset;
automatically co-register the first labeled dataset and the second labeled dataset to each other to generate a transformation matrix based on the first labeled dataset and the second labeled dataset; and
apply the transformation matrix to align the first dataset and the second dataset.

7. The non-transitory computer-readable medium of claim 6, wherein:
the single subject brain comprises a cerebrospinal fluid region;
the first imaging scan is a contrast weighted scan and the first dataset is a contrast weighted dataset; and
the instructions are executable by the one or more processors to:
select, based on the labeled dataset, voxels of the first dataset identified as belonging to the cerebrospinal fluid region;
apply a filtering algorithm to identify voxels of the first dataset representing blood vessels and assign a vesselness weight value to each voxel;
integrate the vesselness weight values into the first dataset; and
after aligning the first dataset and the second dataset, convert the first dataset to a surface anatomical mesh model.

8. The non-transitory computer-readable medium of claim 6, wherein the adaptive segmentation algorithm assigns a numeric label value to each voxel of the first dataset or the second dataset.

9. The non-transitory computer-readable medium of claim 6, wherein:
the first imaging scan is a contrast weighted scan and the second imaging scan is an anatomical scan; and
the instructions are executable by the one or more processors to:
define predicted target point coordinates and entry point coordinates for a probe based on target point coordinates and entry point coordinates of previously implanted probes or by user defined target and entry points;
define a trajectory for the probe based on a mean target coordinates and mean entry point coordinates;
adjust the trajectory to intersect with a nearest voxel assigned a label of an anatomical region of interest;
check proximity of the trajectory to critical structures based on user defined constraints and/or user defined modification of the trajectory to satisfy the user defined constraints; and
superimpose the trajectory on the second data set to form a planning dataset.

10. The non-transitory computer-readable medium of claim 6, wherein:
the first imaging scan is an anatomical scan, the second imaging scan is a post-implantation imaging scan, the first dataset is an anatomical dataset, and the second dataset is a post-implantation dataset; and
the instructions are executable by the one or more processors to:
obtain a third imaging scan used to guide electrode implantation during surgery;
convert the third imaging scan to a third dataset;
align a third dataset with the first dataset;
obtain a trajectory implant data file created during the electrode implantation;
generate a planned trajectory dataset, based on trajectory implant data file, that includes dummy objects disposed at locations of electrode geometry;
align the planned trajectory dataset to the post-implantation dataset; and
automatically identify and label electrodes in an electrode dataset based on the dummy objects of the trajectory implant data file.

11. A system, comprising:
one or more processors; and
a memory coupled to the one or more processors, wherein the memory stores instructions that configure the one or more processors to:
obtain a first imaging scan and a second imaging scan of a subject brain;
convert the first imaging scan to a first dataset, and the second imaging scan to a second dataset;
apply an adaptive segmentation algorithm to the first dataset and the second dataset, wherein the adaptive segmentation algorithm performs automatic intensity-based tissue classification to generate a first labeled dataset and a second labeled dataset;
automatically co-register the first labeled dataset and the second labeled dataset to each other to generate a transformation matrix based on the first labeled dataset and the second labeled dataset; and
apply the transformation matrix to align the first dataset and the second dataset.

12. The system of claim 11, wherein:
the single subject brain comprises a cerebrospinal fluid region;
the first imaging scan is a contrast weighted scan and the first dataset is a contrast weighted dataset; and
the instructions configure the one or more processors to:
select, based on the labeled dataset, voxels of the first dataset identified as belonging to the cerebrospinal fluid region;

apply a filtering algorithm to identify voxels of the first dataset representing blood vessels and assign a vesselness weight value to each voxel;

integrate the vesselness weight values into the first dataset; and after aligning the first dataset and the second dataset, convert the first dataset to a surface anatomical mesh model.

13. The system of claim 11, wherein the adaptive segmentation algorithm assigns a numeric label value to each voxel of the first dataset or the second dataset.

14. The system of claim 11, wherein the instructions configure the one or more processors to:

extract voxels from the first dataset having a label corresponding to a subcortical region of interest;

form a third dataset containing the voxels extracted from the first dataset;

convert the third dataset into a first subcortical surface mesh model;

compute curvature and sulcal features of the first subcortical surface mesh model;

align the first subcortical surface mesh model to a subcortical atlas of the region of interest using the curvature and sulcal features; and overlay the first subcortical surface mesh model aligned to an atlas of the subcortical region of interest on a second subcortical surface mesh model, the second subcortical surface mesh model having a standardized number of nodes that enables a one-to-one correspondence between node identity and atlas location; and assign coordinates of nodes of the first subcortical surface mesh model to the second subcortical structure surface mesh model such that the second subcortical surface mesh model assumes a topology of the first subcortical structure surface mesh model.

15. The system of claim 11, wherein:

the first imaging scan is a contrast weighted scan and the second imaging scan is an anatomical scan; and the instructions configure the one or more processors to:

define predicted target point coordinates and entry point coordinates for a probe based on target point coordinates and entry point coordinates of previously implanted probes or by user defined target and entry points;

define a trajectory for the probe based on a mean target coordinates and mean entry point coordinates;

adjust the trajectory to intersect with a nearest voxel assigned a label of an anatomical region of interest;

check proximity of the trajectory to critical structures based on user defined constraints and/or user defined modification of the trajectory to satisfy the user defined constraints; and superimpose the trajectory on the second data set to form a planning dataset.

16. The system of claim 11, wherein:

the first imaging scan is an anatomical scan, the second imaging scan is a post-implantation imaging scan, the first dataset is an anatomical dataset, and the second dataset is a post-implantation imaging dataset; and the instructions configure the one or more processors to:

obtain a third imaging scan used to guide electrode implantation during surgery;

convert the third imaging scan to a third dataset;

align a third dataset with the first dataset;

obtain a trajectory implant data file created during the electrode implantation;

generate a planned trajectory dataset, wherein:

the planned trajectory dataset is based on trajectory implant data file; and the planned trajectory dataset includes dummy objects disposed at locations of electrode geometry;

align the planned trajectory dataset to the post-implantation imaging dataset; and identify electrodes in an electrode dataset based on the dummy objects of the trajectory implant data file.

* * * * *